United States Patent
Sutherland et al.

(10) Patent No.: US 10,433,960 B1
(45) Date of Patent: Oct. 8, 2019

(54) METHOD AND SYSTEM FOR TRANSCATHETER INTERVENTION

(71) Applicant: CardioPrecision Limited, Glasgow (GB)

(72) Inventors: Fraser William Havern Sutherland, Glasgow (GB); Ying Sutherland, Glasgow (GB)

(73) Assignee: CardioPrecision Limited, Glasgow (GB)

( * ) Notice: Subject to any disclaimer, the term of this patent is extended or adjusted under 35 U.S.C. 154(b) by 113 days.

(21) Appl. No.: 15/148,749

(22) Filed: May 6, 2016

Related U.S. Application Data

(60) Provisional application No. 62/158,160, filed on May 7, 2015.

(51) Int. Cl.
| | | |
|---|---|---|
| *A61F 2/24* | (2006.01) | |
| *A61B 17/34* | (2006.01) | |
| *A61M 25/09* | (2006.01) | |
| *A61M 25/04* | (2006.01) | |

(52) U.S. Cl.
CPC ........ *A61F 2/2427* (2013.01); *A61B 17/3415* (2013.01); *A61B 17/3478* (2013.01); *A61M 25/04* (2013.01); *A61M 25/09* (2013.01)

(58) Field of Classification Search
CPC . A61B 90/35; A61B 17/0218; A61B 17/0469; A61F 2/2427
See application file for complete search history.

(56) References Cited

U.S. PATENT DOCUMENTS

| | | | |
|---|---|---|---|
| 4,091,612 | A | 5/1978 | Meisner et al. |
| D248,870 | S | 8/1978 | Hass |
| 4,562,832 | A | 1/1986 | Wilder et al. |
| 4,616,633 | A | 10/1986 | Vargas Garcia |
| 4,702,230 | A | 10/1987 | Pelta |
| 5,200,939 | A | 4/1993 | Nishiwaki et al. |
| 5,634,883 | A | 6/1997 | Chin et al. |
| 5,676,636 | A | 10/1997 | Chin |
| 5,941,819 | A | 8/1999 | Chin |
| 5,967,971 | A | 10/1999 | Bolser |

(Continued)

FOREIGN PATENT DOCUMENTS

| | | |
|---|---|---|
| DE | 19629304 A1 | 1/1998 |
| DE | 202004001136 U1 | 4/2004 |

(Continued)

OTHER PUBLICATIONS

Ohtsuka, Toshiya, "Sternum lifting technique for thoracoscopic internal thoracic artery harvest", European Journal of Cardio-Thoracic Surgery, 2005, (5 pages).

(Continued)

*Primary Examiner* — Thomas M McEvoy
(74) *Attorney, Agent, or Firm* — Winstead PC

(57) ABSTRACT

A method for accessing a mitral valve that includes forming an incision and inserting a first catheter comprising a lumen. The first catheter is adapted to be directed towards a left atrium and the first catheter has a working length of approximately 15 cm to approximately 52 cm. The method further includes utilizing a trocar in the first catheter to penetrate a pericardium and utilizing the trocar to penetrate the left atrium. The method further includes accessing the mitral valve from an antegrade direction.

10 Claims, 18 Drawing Sheets

(56) References Cited

U.S. PATENT DOCUMENTS

| | | | |
|---|---|---|---|
| 6,015,378 A | 1/2000 | Borst et al. | |
| 6,106,497 A | 8/2000 | Wang | |
| D433,134 S | 10/2000 | Pitesky | |
| 6,159,231 A | 12/2000 | Looney et al. | |
| 6,274,859 B1 | 8/2001 | Yoshino et al. | |
| 6,347,168 B1 | 2/2002 | Shimomura et al. | |
| 6,355,030 B1 | 3/2002 | Aldrich et al. | |
| 6,522,794 B1 | 2/2003 | Bischel et al. | |
| 6,965,710 B2 | 11/2005 | Makio | |
| D522,140 S | 5/2006 | Stalcup et al. | |
| D523,142 S | 6/2006 | Stalcup et al. | |
| 7,194,153 B1 | 3/2007 | Yajima et al. | |
| D568,471 S | 5/2008 | Engler | |
| D586,914 S | 2/2009 | DaSilva | |
| D589,145 S | 3/2009 | Miller | |
| D658,286 S | 4/2012 | Ryshkus et al. | |
| D669,171 S | 10/2012 | Boedeker | |
| 8,545,551 B2 | 10/2013 | Loulmet | |
| D724,207 S | 3/2015 | Sutherland et al. | |
| 9,002,159 B2 | 4/2015 | Sutherland et al. | |
| 9,232,886 B2 | 1/2016 | Sutherland et al. | |
| 2001/0005787 A1* | 6/2001 | Oz | A61B 17/064 606/142 |
| 2001/0009971 A1 | 7/2001 | Sherts et al. | |
| 2003/0053744 A1 | 3/2003 | Makio | |
| 2003/0060686 A1 | 3/2003 | Taylor et al. | |
| 2003/0095781 A1 | 5/2003 | Williams | |
| 2004/0138685 A1 | 7/2004 | Clague et al. | |
| 2004/0242968 A1 | 12/2004 | Hill et al. | |
| 2004/0260366 A1 | 12/2004 | Svanberg et al. | |
| 2005/0041909 A1 | 2/2005 | Nakano et al. | |
| 2005/0092333 A1 | 5/2005 | Cosgrove | |
| 2005/0119530 A1 | 6/2005 | Douglas et al. | |
| 2005/0159650 A1 | 7/2005 | Raymond et al. | |
| 2006/0217596 A1 | 9/2006 | Williams | |
| 2006/0217597 A1 | 9/2006 | Vayser et al. | |
| 2007/0112256 A1 | 5/2007 | Terakawa et al. | |
| 2007/0129608 A1 | 6/2007 | Sandhu | |
| 2007/0238932 A1 | 10/2007 | Jones et al. | |
| 2007/0263173 A1 | 11/2007 | Reimer et al. | |
| 2008/0002426 A1 | 1/2008 | Vayser et al. | |
| 2008/0113312 A1 | 5/2008 | Ortega | |
| 2009/0244905 A1 | 10/2009 | Ishida et al. | |
| 2010/0312069 A1 | 12/2010 | Sutherland et al. | |
| 2012/0078353 A1 | 3/2012 | Quadri et al. | |
| 2012/0116418 A1* | 5/2012 | Belson | A61B 17/0469 606/139 |
| 2012/0154912 A1 | 6/2012 | Shihoh | |
| 2013/0053950 A1 | 2/2013 | Rowe et al. | |
| 2013/0155723 A1 | 6/2013 | Coleman | |
| 2013/0267785 A1 | 10/2013 | Sutherland et al. | |
| 2014/0128141 A1 | 5/2014 | Bontempo et al. | |

FOREIGN PATENT DOCUMENTS

| | | |
|---|---|---|
| EP | 0101781 A1 | 3/1984 |
| EP | 0856286 A1 | 8/1998 |
| EP | 0993579 A1 | 4/2000 |
| EP | 1690498 A2 | 8/2006 |
| GB | 2133694 A | 8/1984 |
| JP | H01159615 A | 6/1989 |
| JP | H04268528 A | 9/1992 |
| JP | H04277423 A | 10/1992 |
| JP | H05273476 A | 10/1993 |
| JP | 07-136173 | 5/1995 |
| JP | 08-071073 | 3/1996 |
| JP | H10108824 A | 4/1998 |
| JP | 10277043 A | 10/1998 |
| JP | 3056375 U | 2/1999 |
| JP | H11511366 A | 10/1999 |
| JP | 2000007291 A | 1/2000 |
| JP | 2000166930 A | 6/2000 |
| JP | 2001042401 A | 2/2001 |
| JP | 2006156138 A | 6/2006 |
| SU | 1482675 A1 | 5/1989 |
| WO | WO-97/10753 A1 | 3/1997 |
| WO | WO-9923935 A1 | 5/1999 |
| WO | WO-0015116 A1 | 3/2000 |
| WO | WO-03/017847 A1 | 3/2003 |
| WO | WO-2004/044632 A1 | 5/2004 |
| WO | WO-2007084641 A2 | 7/2007 |
| WO | WO-2009/090383 A2 | 7/2009 |
| WO | WO-2012/038714 A1 | 3/2012 |
| WO | WO-2014/064694 A2 | 5/2014 |

OTHER PUBLICATIONS

Lamelas, Joseph Intercostal Retractor System, "Miami Method Tailor-Made Exposure Products," Next Generation MICS Instrumentation, 2013, 5 pages.

Plass, Andre, et al., "Aortic Valve Replacement Through a Minimally Invasive Approach: Preoperative Planning, Surgical Technique, and Outcome," The Society of Thoracic Surgeons, 2009, 6 pages.

Aesculap, "Valve XS: Instruments for Minimally Invasive Valve Surgery," Aesculap Surgical Technologies—Surgical Instruments, 2010, 27 pages.

Abdel-Wahab, Mohamed, et al.; "Update on Transcatheter Aortic Valve Replacement"; Trends in Cardiovascular Medicine, vol. 25, Issue 2; Feb. 2015; pp. 154-161.

Ampollini, Luca, et al.; "Transcervical Video-Assisted Thymectomy: Preliminary Results of a Modified Surgical Approach"; Langenbeck's Archive of Surgery, vol. 396, Issue 2; Dec. 30, 2010; pp. 267-271.

Babaliaros, Vasilis, et al.; "Comparison of Transfemoral Transcatheter Aortic Valve Replacement Performed in the Catheterization Laboratory (Minimalist Approach) versus Hybrid Operating Room (Standard Approach)"; JACC: Cardiovascular Interventions, vol. 7, No. 8; Aug. 2014; pp. 898-904.

Biancari, Fausto, et al.; "Immediate Outcome after Sutureless versus Transcatheter Aortic Valve Replacement"; Heart Vessels; Jan. 9, 2015; pp. 1-7.

Bramis, J., et al.; "Video-Assisted Transcervical Thymectomy"; Surg Endosc, vol. 18; Aug. 26, 2004; pp. 1535-1538.

Brown, Morgan L., et al.; "Ministernotomy versus Conventional Sternotomy for Aortic Valve Replacement: A Systematic Review and Meta-Analysis"; J Thorac Cardiovasc Surg, vol. 137, No. 3; Mar. 2009; pp. 670-679.

Byrne, John G., et al.; "Minimally Invasive Direct Access Heart Valve Surgery"; J Card Surg, vol. 15, No. 1; Jan. 2000; pp. 21-34.

Calhoun, Royce F., et al.; "Results of Transcervical Thymectomy for Myasthenia Gravis in 100 Consecutive Patients"; Annals of Surgery, vol. 230, No. 4; Apr. 15, 1999; pp. 555-561.

Clavel, Marie-Annick, et al.; "Validation and Characterization of Transcatheter Aortic Valve Effective Orifice Area Measured by Doppler Echocardiography"; JACC: Cardiovascular Imaging, vol. 4, No. 10; Oct. 2011; pp. 1053-1062.

Cooper, J.D., et al.; "An Improved Technique to Facilitate Transcervical Thymectomy for Myasthenia Gravis"; Ann Thorac Surg, vol. 45; Sep. 21, 1987; pp. 242-247.

Cosgrove, Delos M., et al.; "Minimally Invasive Approach for Aortic Valve Operations"; Ann Thorac Surg, vol. 62; Apr. 1996; pp. 596-597.

Czesla, Markus, et al.; "Safeguards and Pitfalls in Minimally Invasive Mitral Valve Surgery"; Ann Cardiothorac Surg, vol. 2, No. 6; Nov. 2013; pp. 849-852.

De Perrot, Marc, et al.; "Impact of Minimally Invasive Trans-Cervical Thymectomy on Outcome in Patients with Myasthenia Gravis"; Eur J Cardiothorac Surg, vol. 24, No. 5; Nov. 2003; pp. 677-683.

Deeb, Maher E., et al.; "Expanded Indications for Transcervical Thymectomy in the Management of Anterior Mediastinal Masses"; Ann Thorac Surg, vol. 72, No. 1; Jul. 2001; pp. 208-211.

Doss, M., et al.; "Sutureless Aortic Valve Replacement: Catheter-Based Transapical versus Direct Transaortic Implantation"; J Heart Valve Dis, vol. 21, No. 6; Nov. 2012; pp. 758-763 (abstract only, 2 pages).

(56) References Cited

OTHER PUBLICATIONS

Drews, Thorsten, et al.; "Elective Femoro-Femoral Cardiopulmonary Bypass during Transcatheter Aortic Valve Implantation: A Useful Tool"; J Thorac Cardiovasc Surg, vol. 145, No. 3; Mar. 12, 2012; pp. 757-763.
Ewe, See Hooi, et al.; "Location and Severity of Aortic Valve Calcium and Implications for Aortic Regurgitation after Transcatheter Aortic Valve Implantation"; Am J Cardiol, vol. 108, No. 10; Aug. 17, 2011; pp. 1470-1477.
Généreux, Philippe, et al.; "Paravalvular Leak after Transcatheter Aortic Valve Replacement"; J Am Coll Cardiol, vol. 61, No. 11; Mar. 19, 2013; pp. 1125-1136.
Glauber Mattia, et al.; "Minimally Invasive Aortic Valve Surgery: State of the Art and Future Directions"; Ann Cardiothorac Surg, vol. 4, No. 1; Jan. 2015; pp. 26-32.
Glauber, Mattia, et al.; "Minimally Invasive Aortic Valve Replacement via Right Anterior Minithoracotomy: Early Outcomes and Midterm Follow-Up"; J Thorac Cardiovasc Surg, vol. 142, No. 6; Jul. 4, 2011; pp. 1577-1579.
Gopaldas, RR, et al.; "Why Choose Cardiothoracic Surgery as a Career?"; Heart Surg Forum, vol. 14, No. 3; Jun. 2011; pp. E142-148 (abstract only, 2 pages).
Grossi, Eugene A., et al.; "Comparison of Post-Operative Pain, Stress Response, and Quality of Life in Port Access vs. Standard Sternotomy Coronary Bypass Patients"; Eur J Cardiothorac Surg, vol. 16 (Suppl. 2); Nov. 1999; S39-S42.
Gundry, Steven R., et al.; "Facile Minimally Invasive Cardiac Surgery via Ministernotomy"; Ann Thorac Surg, vol. 65, No. 4; Feb. 3, 1997; pp. 1100-1104.
Healy, Samuel E., et al.; "Thiel Embalming Method for Cadaver Preservation: A Review of New Training Model for Urologic Skills Training"; Urology, vol. 85, Issue. 3; Mar. 2015; pp. 499-504.
Huang, CS, et al.; "Factors Influencing the Outcome of Transsternal Thymectomy for Myasthenia Gravis"; Acta Neurol Scand, vol. 112, Issue 2; May 26, 2005; pp. 108-114.
Kappetein, A. Pieter, et al.; "Updated Standardized Endpoint Definitions for Transcatheter Aortic Valve Implantation: The Valve Academic Research Consortium-2 Consensus Document"; J Thorac Cardiovasc Surg, vol. 145, No. 1; Oct. 16, 2012; pp. 6-23.
Kas, József, et al.; "Decade-Long Experience with Surgical Therapy of Myasthenia Gravis: Early Complications of 324 Transsternal Thymectomies"; Ann Thorac Surg, vol. 72, Issue 5; Nov. 2001; pp. 1691-1697.
Khoshbin, E., et al.; "Mini-Sternotomy for Aortic Valve Replacement reduces the Length of Stay in the Cardiac Intensive Care Unit: Meta-Analysis of Randomised Controlled Trials"; BMJ Open, vol. 1, No. 2; Nov. 24, 2011; pp. 1-5.
Kiser, Andy C., et al.; "Suprasternal Direct Aortic Approach Transcatheter Aortic Valve Replacement Avoids Sternotomy and Thoracotomy: First-in-Man Experience"; Eur J Cardiothorac Surg, vol. 48, Issue 5; Oct. 2014; 7 pages.
Leon, Martin B., et al.; "Standardized Endpoint Definitions for Transcatheter Aortic Valve Implantation Clinical Trials: A Consensus Report from the Valve Academic Research Consortium"; Eur Heart J, vol. 32, No. 2; Jan. 6, 2011; pp. 205-217.
Mangner, Norman, et al.; "Remaining Pitfalls and Limitations of TAVI in 2014"; EuroIntervention, vol. 10; Sep. 2014; pp. U35-U43.
Murtuza, Bari, et al.; "Minimal Access Aortic Valve Replacements: Is It Worth It?"; Ann Thorac Surg, vol. 85, Issue 3; Mar. 2008; pp. 1121-1131.

Noad, Rebecca L., et al.; "A Pathway to Earlier Discharge Following TAVI: Assessment of Safety and Resource Utilization"; Catheterization and Cardiovascular Interventions, vol. 87, Issue 1; May 23, 2015; pp. 134-142.
O'Sullivan, Katie E., et al.; "Transaortic Tavi is a Valid Alternative to Transapical Approach"; J Card Surg, vol. 30, Issue 5; Mar. 10, 2015; pp. 381-390.
Permanyer, Eduard, et al.; "The 3f Enable Sutureless Bioprosthesis: Early Results, Safeguards, and Pitfalls"; J Thorac Cardiovasc Surg, vol. 149, No. 6; Oct. 15, 2014; pp. 1578-1583.
Phan, Kevin, et al.; "A Meta-Analysis of Minimally Invasive versus Conventional Sternotomy for Aortic Valve Replacement"; Ann Thorac Surg, vol. 98, Issue 4; Oct. 2014; pp. 1499-1511.
Rogers, Chris A., et al.; "An Open Randomized Controlled Trial of Median Sternotomy versus Anterolateral Left Thoracotomy on Morbidity and Health Care Resource Use in Patients Having Off-Pump Coronary Artery Bypass Surgery: The Sternotomy versus Thoracotomy (STET) Trial"; J Thorac Cardiovasc Surg, vol. 146, No. 2; Aug. 2013; pp. 306-316.
Roy, David A., et al.; "Transcatheter Aortic Valve Implantation for Pure Severe Native Aortic Valve Regurgitation"; J Am Coll Cardiol, vol. 61, No. 15; Feb. 20, 2013; pp. 1577-1584.
Schroeyers, Pascal, et al.; "Minimally Invasive Video-Assisted Mitral Valve Surgery: Our Lessons after a 4-Year Experience"; Ann Thorac Surg, vol. 72, Issue 3; Sep. 2001; pp. S1050-S1054.
Shrager, Joseph B., et al.; "Transcervical Thymectomy for Myasthenia Gravis Achieves Results Comparable to Thymectomy by Sternotomy"; Ann Thorac Surg, vol. 74, No. 2; Jan. 28, 2002; pp. 320-327.
Shrager, Joseph B., et al.; "Outcomes after 151 Extended Transcervical Thymectomies for Myasthenia Gravis"; Ann Thorac Surg, vol. 82, Issue 5; Nov. 2006; pp. 1863-1869.
Shrager, Joseph B.; "Extended Transcervical Thymectomy: The Ultimate Minimally Invasive Approach"; Ann Thorac Surg, vol. 89, No. 6; May 20, 2010; pp. S2128-S2134.
Thourani, Vinod H., et al.; "Use of Transaortic, Transapical, and Transcarotid Transcatheter Aortic Valve Replacement in Inoperable Patients"; Ann Thorac Surg, vol. 96, No. 4; Aug. 21, 2013; pp. 1349-1357.
Wong, Dennis T.L., et al.; "Relationship of Aortic Annular Eccentricity and Paravalvular Regurgitation Post Transcatheter Aortic Valve Implantation with CoreValve"; J Invasive Cardiol, vol. 25, No. 4; Apr. 2013; pp. 190-195.
Zannis, Konstantinos, et al.; "New Sutureless Aortic Valve Prosthesis: Another Tool in Less Invasive Aortic Valve Replacement"; Curr Opin Cardiol, vol. 27, Issue 2; Mar. 2012; pp. 125-129.
Lannemyr, Lukas, et al., Effects of Cardiopulmonary Bypass on Renal Perfusion, Filtration, and Oxygenation in Patients Undergoing Cardiac Surgery, Anesthesiology, vol. 126, No. 2, pp. 205-213 (2017).
Research and Markets: Endovascular Thoracic Aortic Aneurysm Repair Device Market 2010 Edition—Technology Update & Market Forecast, MedTech Report (2010) [3 pages].
National Patient Safety Agency, Patient Safety Division, Supporting Information, Rapid Response Report: Risk of chest drain insertion, Reference NPSA/2008/RRR03 (May 2008) [10 pages].
American College of Surgeons, the Advanced Trauma Life Support (ATLS) Course Manual, Ninth Ed. (2012) [392 pages].

\* cited by examiner

METHOD AND SYSTEM FOR TRANSCATHETER INTERVENTION

CROSS-REFERENCE TO RELATED APPLICATIONS

This patent application claims priority to, and incorporates by reference for any purpose the entire disclosure of, U.S. Provisional Patent Application No. 62/158,160, filed May 7, 2015. U.S. Pat. No. 9,232,886, filed Jan. 15, 2009, U.S. Pat. No. 9,002,159, filed Aug. 30, 2011, and U.S. patent application Ser. No. 13/826,750, filed Mar. 14, 2013, are incorporated herein by reference.

BACKGROUND

Field of the Invention

The present application relates generally to cardiac interventions and more particularly, but not by way of limitation, to methods and systems for providing access to the left atrium to perform percutaneous or transcatheter intervention on the mitral valve of the heart. The present invention also relates to methods and systems for providing access to the aorta to perform endovascular repair of the thoracic or abdominal aorta.

History of the Related Art

Mitral Valve Disease

Heart disease is a disease of increasing age and the projected shift to an older population will likely increase the societal burden of heart disease substantially in the future. The most common pathology seen in heart disease is mitral regurgitation with more than 9.3% of the US population over the age of 75 exhibiting mitral regurgitation.

SUMMARY

The present application relates generally to cardiac interventions and more particularly, but not by way of limitation, to methods and systems for providing access to the left atrium to perform percutaneous or transcatheter intervention on the mitral valve of the heart. In one aspect, the present invention relates to a catheter system. The catheter system includes an inner catheter having a mating feature disposed thereon. A hub catheter surrounds the inner catheter. The hub catheter engages with the mating feature to removably secure a mitral valve to the inner catheter. The inner catheter and the hub catheter facilitate deployment of the mitral valve to a left atrium in an antegrade direction. The hub catheter is axially translated relative to the inner catheter to release the valve. The catheter comprises a working length of approximately 15 cm to approximately 52 cm to facilitate delivery of the mitral valve in the antegrade direction.

In another aspect the present invention relates to a method for accessing a mitral valve. The method includes forming an incision and inserting a first catheter comprising a lumen. The first catheter is adapted to be directed towards a left atrium and the first catheter has a working length of approximately 15 cm to approximately 52 cm. The method further includes utilizing a trocar in the first catheter to penetrate a pericardium and utilizing the trocar to penetrate the left atrium. The method further includes accessing the mitral valve from an antegrade direction.

In another aspect, the present invention relates to a method of training a medical practitioner. The method includes observing insertion of a delivery catheter into a left atrium of a patient and verifying placement of the delivery catheter in the left atrium to facilitate antegrade delivery of a valve. The method further includes observing utilization of a trocar to penetrate a pericardium and observing utilization of the trocar to penetrate the left atrium and access a mitral valve from an antegrade direction. The method further includes instructing a student to release the valve by utilizing a second thumb wheel to withdraw a hub catheter. The method further includes confirming proper deployment of the valve and verifying closure of the left atrium.

BRIEF DESCRIPTION OF THE DRAWINGS

For a more complete understanding of the present invention and for further objects and advantages thereof, reference may now be had to the following description taken in conjunction with the accompanying drawings in which.

DETAILED DESCRIPTION

Figure 1:
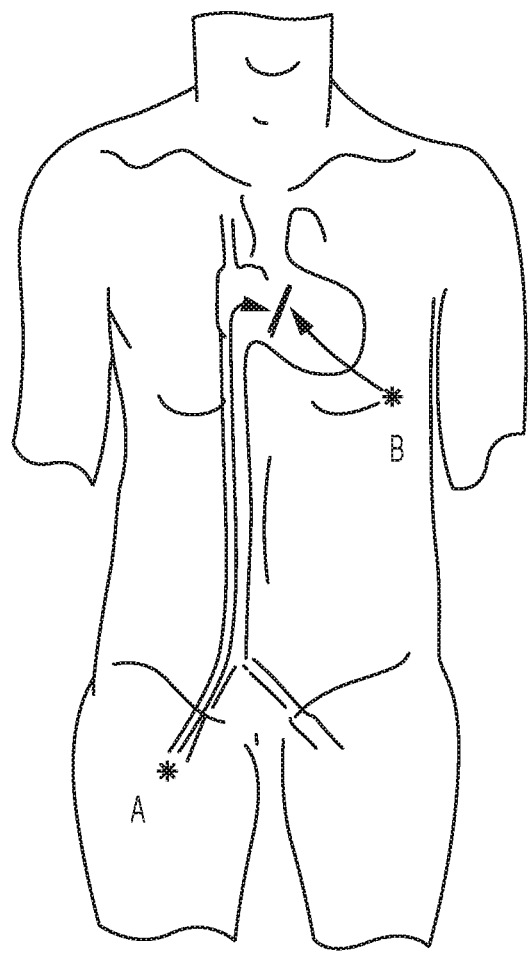
FIG. 1 shows an existing access route for percutaneous mitral valve intervention in Femoral Venous Approach (A) and Trans Apical Approach (B).

Various embodiments of the present invention will now be described more fully with reference to the accompanying drawings. The invention may, however, be embodied in many different forms and should not be construed as limited to the embodiments set forth herein.

In mitral regurgitation a proportion of blood ejected by the left ventricle passes backwards into the left atrium rather than forwards into the aorta. The effect of this is firstly to increase preload on the left ventricle which in turn causes volume overloading of the left ventricle; and secondly to increase pressure in the left atrium which causes enlargement of the left atrium and its appendage. If left untreated, moderate to severe mitral regurgitation can progress to congestive cardiac failure with pulmonary oedema and death. Enlargement of the left atrium and its appendage also predisposes the patient to arrhythmias such as atrial fibrillation and the formation of mural thrombi which may become dislodged and embolize causing stroke or an ischemic event in another body organ.

At present, mitral valve surgery is performed through a median sternotomy incision. This technique is called open mitral valve surgery. The operation entails making a vertical incision on the chest and then splitting the breastbone along its entire length with a saw. The bone is wired together at the end of the procedure. The incision is very invasive, causing substantial pain and typically necessitating at least two days in critical care followed by several days on the surgical ward before discharge home where a further period of recovery is required. In addition blood loss is inevitable during the procedure and there is a risk of major complications such as deep sternal wound infection which complications may prolong or hinder the patient's recovery or even cause death.

To overcome these problems with open surgery, surgeons have performed mitral valve surgery through a serious of small incisions or ports accompanied by an endoscope to provide visualization of the mitral valve. This is called minimally invasive mitral valve surgery. Such minimally invasive surgical procedures still require the patient to be placed on cardiopulmonary bypass and for the left atrium to be opened and for the valve to be repaired or replaced using surgical instruments and standard surgical techniques used in the median sternotomy approach described above. Although the patient is expected to recover more quickly after such minimally invasive mitral valve surgery because of the absence of a median sternotomy incision, recovery still typically entails four or five days stay in a hospital with one or two days in critical care. While the risk of blood loss is less it is not eliminated by minimally invasive surgical approaches. Other risks such as retrograde dissection of the aorta and respiratory complications associated with collapsing the left lung during surgery, which complications are generally not observed after open surgery, are more likely with the minimally invasive surgical approaches currently in use. Therefore, the minimally invasive approaches currently in use do not overcome all of the problems associated with open mitral valve surgery.

Because both open surgery and the current minimally invasive approaches are associated with major risks for the patient, surgical repair is often not an option for certain patients as the risks outweigh the potential benefits. As a result, there is pressing need for alternative procedures for mitral valve surgery which are preferably less invasive, which are associated with fewer complications.

Transcatheter approaches for the aortic valve have progressed much more rapidly than those for the mitral valve. Percutaneous access to the aorta for such transcatheter techniques is achieved by making a puncture wound in one of the femoral arteries which arteries are relatively superficial. Guide wires, catheters and balloons and the aortic valve replacement are then passed through the external iliac artery, the common iliac artery, the abdominal aorta, the descending thoracic aorta, the aortic arch and into the ascending aorta. Thus, the transcatheter technique for aortic valve implantation makes use of a natural anatomical pathway. This is one of the reasons for transcatheter techniques being more advanced for aortic valve replacement.

Unfortunately, there is no such natural anatomical pathway to reach the mitral valve. The mitral valve is located between the left atrium and left ventricle. The left atrium is located deep within the chest. Therefore, direct puncture of the left atrium is not possible percutaneously. The tributaries of the left atrium, and the right and left superior and inferior pulmonary veins also lie deep within the chest making them inaccessible.

Diseases Affecting the Aorta

The aorta is the main artery leaving the heart and distributes blood to the entire body. For descriptive purposes, the aorta is divided into two sections the thoracic aorta and the abdominal aorta, which are separated by the diaphragm. This is explained below with reference to FIG. 8.

The thoracic portion of the aorta includes an ascending section that arises from the heart and extends several inches from the heart into the aortic arch. The first branch of the aortic arch is the brachiocephalic trunk which divides into right common carotid and right subclavian arteries. The second branch is typically the left common carotid artery followed by the left subclavian artery. Several other well described anatomical variants occur less commonly.

The aortic arch gives rise to the descending thoracic aorta after the left subclavian artery. This vessel descends towards the abdomen. The abdominal portion of the aorta begins below the diaphragm. The renal arteries are important branches which feed the kidneys on each side. The aorta is thus split into suprarenal (above the renal arteries) and infrarenal sections, for the purposes of description.

Further down, the aorta divides at the iliac bifurcation into the two common iliac arteries that feed the pelvis and legs. The common iliac artery on each side branches into internal and external iliac arteries. The external iliac arteries are larger than the internal iliac arteries. They change their name to the femoral arteries as they emerge from behind the inguinal ligament on each side and provide blood to the lower extremities. Different sections of the aorta are susceptible to different diseases; and because the aorta handles blood under extremely high pressures, injury or disease can be fatal.

Thoracic aortic disease can take several forms, including thoracic aortic aneurysms, pseudo aneurysms, aortic dissections, intra mural haematoma, penetrating ulcers and trauma. An aortic aneurysm is the natural ballooning of the aorta due to high blood pressure and results in a weakened vessel wall. A pseudo aneurysm refers to a localized swelling the tissue adjacent to the aorta due to transmural lacerations in the aorta, which are often caused by blunt trauma but may arise following previous surgical intervention. Aortic dissection refers to a tear in the inner layer of the aorta that allows blood to enter and separate the inner and outer layers of the aorta. Aortic dissections can be classified by the commonly used Stanford classification into two groups according to whether or not the ascending aorta is involved. Stanford Type A dissection of the aorta involves the ascending aorta and/or the aortic arch, and possibly the descending aorta. The tear can originate in the ascending aorta, the aortic arch, or, more rarely, in the descending aorta. Stanford Type B dissection of the aorta involves the descending thoracic aorta or the arch (distal to the left subclavian artery), without involvement of the ascending aorta. The classification allows the extent of the dissection to be described concisely and guides treatment options. An intramural haematoma is similar to an aortic dissection in that haemorrhage occurs between the inner and outer layers of the aorta. However, in an intramural haematoma there is no evidence of visible tear in the inner aortic layer. Penetrating ulcers may occur in atherosclerotic plaques and can penetrate deep into the arterial wall. The descending thoracic aorta just below the left subclavian artery is extremely susceptible to trauma, especially from the rapid acceleration of a pedestrian hit by a car or the rapid deceleration associated with an automobile crash. Laceration of the aorta occurs causing partial or complete transection of the aorta. In general, all of these pathologies merit interventional treatment where possible as the natural history of the untreated conditions is aortic rupture and death.

The abdominal aorta can be affected by diseases such as dissections, intramural hematomas, penetrating ulcers and trauma. By far the most significant risk is aneurysm, the bulging of a weakened area of a blood vessel or artery. The abdominal aorta is especially susceptible to aneurysms above the iliac bifurcation. Such aneurysms of the abdominal aorta (AAA) may present as pulsatile abdominal masses with minor discomfort, as incidental findings or detected during screening. However, a significant proportion of abdominal aortic aneurysms first present with symptoms and signs of rupture. It is estimated that only 10 to 25% of patients who make it to the hospital with a ruptured AAA survive. Evidence of rupture of an AAA merits emergency surgical intervention. Time is of the essence so it is common for patients to be rushed from the emergency room to the operating theatre for intervention as soon as the diagnosis is suspected. Once inside the operating theatre, sudden exsanguination and death is still possible until control of the aorta or definitive repair has been achieved. If the AAA is diagnosed before symptoms or signs of rupture have occurred then elective intervention may be considered. Elective repair of AAA is generally recommended when the aneurysm reaches a diameter of 5 to 6 cm or when there is evidence of rapid increase in size as risk of rupture increases sharply with the diameter of the aneurysm or rapid growth. The incidence and prevalence of AAAs continue to grow due to growth in the global elderly population. Risk factors associated with AAAs include age, male gender, smoking, and family history.

The iliac bifurcation is also susceptible to aneurysms. However, occlusive disease, a narrowing or blockage of the arteries can affect also affect the common, internal, or external iliac arteries. This causes disruption to the flow of blood to the lower extremities resulting in a lack of oxygen and other nutrients to these areas, known as "ischemia". Slow onset ischaemia can present with pain on exercise, so called claudication. However, ischaemia can also present suddenly with pain at rest. In such cases, gangrene can develop in a relatively short space of time which can result in the loss of the affected limb or even death. Iliac aneurysms generally merit treatment to avert the risk of rupture or compression of adjacent structures. Occlusive disease of these vessels can sometimes be managed medically. However, a large proportion of patients with occlusive disease of these vessels will require intervention to prevent lower limb ischaemia either electively or as an emergency procedure to save limb and life.

Most treatments for aortic pathologies have traditionally involved open surgery. Open surgery is a major invasive procedure in which a large incision is made in the chest or abdomen in order to access the relevant section of the aorta. The diseased section of aorta is isolated between clamps, excised and then replaced with an artificial tube interposition graft which is typically sewn end to end to the proximal and distal portions the aorta. The circulation is restored by removal of the clamps. When several portions of the aorta are diseased, more extensive replacement of the aorta is required necessitating larger or multiple incisions and sometimes staged procedures. An extensive period of time in hospital and recuperation after discharge is inevitably required with this type of surgery. Hospital stays lasting 1 to 2 weeks and recuperative periods of up to 6 months are common. A variety of complications are possible with open surgical repair. Aside from technical problems that may arise during sewing of the diseased aorta to an artificial tube graft, such as infection, bleeding, false aneurysm formation, dislodgement of fragments of diseased material into the circulation causing embolic ischaemia, there are multiple potential complications associated with performing major invasive surgery in these patient groups, such as major wound dehiscence or infection, respiratory failure, renal failure, stroke or paraplegia depending upon the location of surgery and the age and co-morbidities of the patients being treated.

An alternative to open surgery is to perform the procedure by endovascular means. The goals of endovascular treatment are similar to open surgery: to reduce the long term chance of rupture and restore flow to distal organs. However, endovascular treatments are generally considered to be less invasive because they do not entail major incision in the abdomen or chest. As a consequence, patients are expected to recover more quickly and with less risk of many, but not all, of the complications associated with open surgery. This is because there are a number of potential complications that are peculiar to patients that have been treated with endovascular stent grafts that are not seen after open surgery. These include endoleaks and access site complications such as pseudoaneurysm formation.

Endoleaks occur when an aneurysmal sac continues to be pressurized despite endoluminal stent placement. Five types of endoleaks are recognized. A type 1 endoleak is caused by inadequate seal at the graft ends. This is most common after repair of thoracic aortic aneurysm using stent grafts but can also occur in the abdominal aorta. These may be further classified by location into type 1a endoleaks at the proximal end, type 1b endoleaks at the distal end and type 1c endoleaks occur in an iliac occluder. Type 2 endoleak occurs when the aneurysmal sac remains filled via a branch vessel, such as the lumbar or inferior mesenteric arteries in the abdominal portion of the aorta. This is most common after repair of abdominal aortic aneurysms and is sometimes referred to as a "retroleak". It may be further classified according to the number of culprit vessels, type 2a being caused by a single vessel and type 2b by two or more vessels. Type 3 endoleaks occur through a defect in the graft fabric. This is a mechanical failure of graft and may either be caused by junctional separation of the modular components *type 3a) or fractures or holes involving the endograft (type 3b). Type 4 endoleaks are caused by a generally porous graft. Type 4 endoleaks are an intentional design of the graft and are not considered a complication. Type 5 endoleaks, also known as "endotension", are not true leaks but defined by the continued expansion of the aneurysm sac greater than 5 mm, without evidence of a leak site. It is a poorly understood phenomenon but thought to be formation of a transudate due to ultrafiltration of blood by the graft membrane or unidentified leak. Type 1 endoleaks are of particular importance because they can occur when the stent graft has not been placed accurately, especially when landing zones are short or affected by diseased aorta.

Surgical procedures have existed for long before the more modern endovascular alternatives and there is abundant evidence demonstrating successful long term outcomes with these treatments. Therefore, until recently, open surgery has been preferred for younger, healthier patients because long term results are proven and trusted; whereas the endovascular alternative has been reserved for older patients or those with significant co-morbidities where surgical risk is prohibitively high. However, patients are becoming more aware and informed of their treatment options and technical success along with other favorable clinical outcomes with the endovascular treatments which are becoming more certain. Hence, increasingly endovascular procedures are being considered as the preferred mode of treatment by both physicians and their patients.

Currently, it is estimated that around 35,000 open surgery and endovascular interventions are performed every year in the developed world (MedTech Report 2010). Endovascular Repair of the Abdominal Aorta is called EVAR. Endovascular repair of the thoracic aorta is called TEVAR. Both of these techniques use stents for repair of the aorta which are explained in the next section.

Antegrade fitting means delivery of a medical device along the normal physiological direction of flow of blood through the body. For example, antegrade in relation to the aorta means in a direction away from the heart. Antegrade in relation of the mitral valve means in a direction from the left atrium to the left ventricle Catheters or guides are medical devices that can be inserted into the body to perform surgical procedures. A catheter at its most general is a tube which allows: drainage, the administration of fluids or gases, the insertion of surgical instruments through its lumen and also perform a variety of other tasks. The tube can be rigid or bendable. The tube can be of varying thickness. The tube can be of varying widths and lengths. Catheters come in a variety of diameters and lengths suited to particular methods of medical intervention. Whilst length of catheter is typically measured in units in common usage such as centimeters, the French scale or French gauge system is generally used to measure the size of a catheter for medical use. The French size is a measure of the external diameter of a catheter. It is most often abbreviated as Fr, but may be abbreviated as Fg, Ga, FR or F or as CH or Ch after its inventor, Charriere. An increasing French size corresponds to an increasing external diameter. Catheter sizes used in the medical field range from 3 Fr to 40 Fr.

An example of a specialized catheter designed for use in coronary artery procedures is the Launcher Coronary Artery Guide catheter (Medtronic, Minneapolis, Minn.). This coronary catheter comes in a range of diameters from 5 Fr to 8 Fr. The smallest diameter catheter, 5 Fr is suitable for diagnostic coronary angiography. However, a slightly larger catheter, 6 Fr, is typically required to accommodate the devices used for percutaneous coronary intervention such as during the insertion of coronary stents. Even larger catheters, 7 Fr or 8 Fr, are required for advanced therapeutic maneuvers such as rotational atherectomy due to the need to deliver larger devices, such as burrs, through the lumen of the device to the site of intervention.

The standard overall length coronary catheter is 100 cm and this length is suitable for most coronary diagnostic or interventional procedures. This standard length catheter is designed so that it may be introduced into the circulation from the femoral artery and its tip advanced into the ascending aorta to the level of the coronary arteries. A guide wire is passed through the lumen of the catheter to direct devices to the site of coronary interventions. Some of the guide wire is advanced beyond the tip of the catheter into the patient and some of the guide wire remains outside of the patient for manipulation by the physician. In general, the same length of catheter can be used when the point of access to the circulation is from the radial artery as when it is from the femoral artery because the distance from point of entry to the coronary arteries is similar in both of these routes. However, when specialized procedures on the coronary arteries are performed that require much greater length of the guide wire to be advanced inside the patient, such as during retrograde intervention on chronic coronary artery occlusions, then a shorter length of catheter, for example a 90 cm catheter length, may be required by the physician so that he has sufficient length of guide wire outside of the patient for him to manipulate the wire and perform the medical intervention with ease.

These examples serve to demonstrate that the diameter and length of the catheter are designed for particular medical methods. Although overall length is commonly used to describe catheters, a more precise definition of length, the working length may be more useful. For example the CPS Venture Wire Control Catheter (St Jude Medical, St Paul, Minn.) has an overall length of 88 cm but a working length of 70 cm by which is meant the distance from the tip of the catheter to the hub of the handle of the catheter is 70 cm. This length allows the catheter to be used to direct steer and control guide wire access of the coronary arteries from a peripheral entry site radial artery or femoral artery.

By closure device is meant medical devices used to achieve hemostasis of the small hole or entry point remaining in a vascular structure after an endovascular procedure has been performed and the catheter removed. There are many closure devices on the market designed to achieve closure and hemostasis of the entry point. Mechanisms of action take several forms including enhanced compression of the entry point from outside of the vessel, plugs, clips, suture mediated devices and anchoring systems. The VAS-CADE (Cardiva Medical, Sunnyvale, Calif.) is an example of an external compression device. The patch material contained within this device increases substantially in volume from its dry state dimensions when hydrated by exposure to blood thereby providing mechanical hemostasis. The Mynx Cadence System (AccessClosure, Inc, Mountain View, Calif.) is another example of an extravascular sealing device This closure device contains a polyethylene glycol (PEG) based sealant that adheres to the artery by interlocking with the vessel wall and instantly absorbs blood and fluids expanding three to four times its original size. The ExoSeal Vascular Closure Device (Cordis, Fremont, Calif.) is an example of a plug system. It utilizes a bioabsorbable polyglycolic acid plug to close the entry point. The StarClose SE Vascular Closure System (Abbott Vascular, Redwood City, Calif.) is an example of a clip mediated closure system. The system works by placing an extravascular nitinol clip over the entry point to achieve haemostasis.

The Perclose A-T and ProGlide Suture-Mediated Closure Systems and ProStar XL Percutaneous Vascular System (Abbott Vascular, Redwood City, Calif.) are examples of suture mediated closure systems. They permit one or more sutures to be placed through the vessel wall and tied from outside of the wound to close the entry point. The AngioSeal (St. Jude Medical, St. Paul, Minn.) is an example of an anchoring system. This closure device creates a mechanical seal by sandwiching the opening in the vessel wall between a bioabsorbable anchor and a collagen sponge. Although originally developed for closure of the entry point in the femoral artery, the commonest point of entry for endovascular procedures, closure devices have also been developed to close entry points made in other vascular structures such as the left ventricle. An example of a closure device for use in closure of the left ventricle is the Apica Access Stabilization and Closure System (Thoratec Corporation, Pleasanton, Calif.). This is a conical-shaped titanium coil with a cap for complete sealing of an apical access site. This is a non-exhaustive list of commercially available closure devices and brief outline of their mechanisms of action.

By graft is meant a tubular structure made from a material that is impervious to blood that may be used as an artificial replacement conduit for a blood vessel such as the aorta.

By guide wire is meant a thin, usually flexible wire that can be inserted into a blood vessel or chamber of the heart for subsequent insertion of a stiffer or bulkier instrument such as a catheter or as a guide for placement of a larger device or prosthesis, such as a mitral valve prosthesis or mitral valve repair device. A guide wire may act not only as a guide for entry into a vascular structure but also as a guide for onward passage through the heart or vasculature to a certain location for example as a guide through the left atrium to the mitral valve or beyond. A guide wire may take the form of a long and flexible fine spring.

By mitral valve prosthesis is meant a medical device comprising an outer support frame or stent, also called an anchor and a valve portion designed to be deployed in the mitral position of a patient with disease of the native mitral valve. The mitral valve prosthesis having an orientation such that it permits blood to pass freely in one direction but obstructs the flow of blood in the opposite direction. The mitral valve prosthesis being capable of being mounted on a catheter. The outer support frame or stent being either balloon expandable, such as the valve prosthesis disclosed in US 20130053950 A1 or self-expanding, such as valve prosthesis in US 2012/0078353 A1. The outer support frame may be equipped with tethers or anchors to keep the valve in place such as those disclosed in US 20130053950 A1 or US 20120078353, respectively.

By mitral valve repair devices is meant medical devices that are designed to be deployed in the vicinity of the mitral valve to restore the function of the mitral valve. Such devices typically retain most if not all of the native mitral valve leaflets. Examples of mitral valve repair devices include the annuluplasty device disclosed in WO 2014064694 A2 or the repair device for clipping valve leaflets, disclosed in U.S. Pat. No. 8,545,551.

By needle means is meant a hollow tube, needle, configured for use in a medical procedure. Such needle means will typically be made from a hardened material such as stainless steel and capable of sterilization by Ethylene Oxide. Needles are available in a wide range of diameters and lengths. The Stubs scale is used to specify the outside diameter of needles. On this scale, the lowest gauge number corresponds to the largest size. The range of diameters of needles commonly used in medical procedures ranges from 7 gauge to 33 gauge on the Stubs scale. At one end, the needle is typically beveled to create a sharp pointed tip promoting ease of tissue penetration. The needle point may have more than one bevels; for example, it may be configured as lancet point with three bevels. The needle tip may be modified with an anti-coring configuration so that the point cleanly pierces through the atrial wall without coring thereby reducing risk of blocking the needle or embolic material from entering the circulation. At the other end, the needle means may be embedded in a plastic, such as polypropylene, or aluminum hub that may be attached to a syringe barrel by means of a press-fit or twist-on fitting. These are sometimes referred to as "Luer Lock" connections.

Pre-mounted devices are devices supplied by the manufacturer already loaded onto a delivery catheter. Pre-mounting of devices eliminates the time required to mount the device on a catheter so saves the physician time during the medical intervention. Pre-mounting of devices must take account of the necessary orientation of the device at the proposed site of deployment. For example, devices may be pre-mounted for antegrade delivery or for retrograde delivery. Although pre-mounted, it may be possible to remove and reload a previously pre-mounted device on the delivery catheter in the opposite orientation for delivery in the opposite direction.

By trocar is meant a sharp-pointed instrument contained within the lumen of a catheter that is used to penetrate the wall of an anatomical structure and carry the catheter with it through the puncture site. The trocar may have a metal or plastic sharpened tip or non-bladed tip. For example, a thoracic catheter and trocar is typically used to penetrate the chest wall to drain air or fluid from the chest cavity.

Repair devices are devices used in the surgical repair of the heart and/or its associated vessels. Devices include stents and other grafts.

Retrograde fitting means delivery of a medical device AGAINST the normal physiological direction of flow of blood through the body. For example, retrograde in the relation to the aorta means a in a direction TOWARDS from the heart. Retrograde in relation of the mitral valve means in a direction from the left ventricle to the left atrium.

A stent comprises a framework which supports a graft material. The framework may be self-expanding, i.e. the structures are shaped or formed from a material that can be provided with a mechanical memory to return to the structure from a compressed or constricted delivery configuration to an expanded deployed configuration. Different portions of the framework may have different functions so the stent may not have a universal repeating pattern along its length. The framework may also have features such as barbs designed to retain position of the device in vivo. The stent may include a main framework segment that constitutes a trunk section. The trunk section may have openings which allow further stents to be funneled through the trunk section to branches off the aorta, for example, into the iliac arteries.

Percutaneous Approaches to the Mitral Valve

There are two percutaneous approaches to the mitral valve. These are: 1) the Femoral venous approach; and 2) the Trans Apical approach. These are shown in FIG. 1. FIG. 1 indicates the long route to the mitral valve and sharp turn through ninety degrees upon entering the heart with the Femoral Venous Approach (A); and the more direct and shorter route to the mitral valve from entry over the left thorax for the Trans Apical Approach (B) but retrograde and through the left ventricle which is also associated with various problems as explained below.

As shown in FIG. 1, in the Femoral Venous approach (A), the femoral vein is entered at the groin, a guide wire is passed up the inferior vena cava into the right atrium, and then through a fenestration created in the septum between the right and left atria, into the left atrium and then through the mitral valve into the left ventricle. The guide wire turns through approximately ninety degrees in this approach.

Also as shown in FIG. 1, the Trans-Apical approach (B) entails making an incision over the left lateral thorax where the left ventricle comes into close proximity with the chest wall. Nevertheless, dissection through the soft tissues and rib spreading with a chest retractor may be required to secure adequate access to the left ventricular apex for the next step. A purse string suture must then be placed in or adjacent to the apex of the left ventricle. The guide wire is passed through the center of the purse string into the left ventricle where it is passed through the mitral valve in a retrograde direction into the left atrium.

In a typical embodiment, an access route for percutaneous transcatheter mitral valve intervention meets the following six criteria:

1. It should follow a smooth curve from point of entry to the mitral valve itself so that devices may be easily passed along a guide wire placed along this route. This is also required so that the guide wire may be easily manipulated. This is especially true for interventional devices such as heart valve prostheses which are likely to be larger than the Mitraclip so difficult to pass around abrupt angulation of the guide wire. Ease of guide wire manipulation is also essential so that the transcatheter heart valve prosthesis may be accurately positioned for optimal performance.

2. It should enter the heart or circulation through a low pressure chamber or vessel so that the entry site may be closed without risk of excessive blood loss and the associated risk of complications from failure to secure the entry site at the end of the procedure. This is especially true for frail elderly patient in whom such complications may lead to death.

3. Approach to the mitral valve should preferably be in an antegrade direction, i.e. with the flow of blood, as unlike the aortic valve, the mitral valve has a complex subvalvar apparatus. Retrograde approach to the mitral valve risks entanglement of guide wires and/or devices in the subvalvar apparatus leading to inadvertent structural damage to the heart, loss of catheter control and possible premature release of devices which may then embolize causing stroke or have to be retrieved by open surgery.

4. The route from skin entry point to mitral valve should be short to facilitate ease of use and accuracy during manipulation of the guide wire.

5. Entry point should preferably be through a clean area of skin i.e. one that is less likely to be colonized by harmful microorganisms to minimize risk of access site infection or contamination of the prosthetic implant device.

6. Entry site must be accessible without causing undue pain or discomfort after the procedure to facilitate rapid recovery and early discharge from hospital.

The inventors have provided four new percutaneous approaches to the mitral valve which, in contrast with the existing Femoral Venous and Trans Apical approaches, meet the 6 criteria set out above. These new approaches are described below and shown in FIGS. 2A and 2B where each 'x' shows an approximate entry point for the different approaches as follows: Suprasternal notch for Transcervical (Suprasternal) approach (1) and Pre-Tracheal Approach (2), right anterior chest such as, for example, in the second or third intercostal space anteriorly for the Right Anterior Approach (3) and entry site on the back to the right of the midline for the Posterior Approach (4).

Figure 2A:
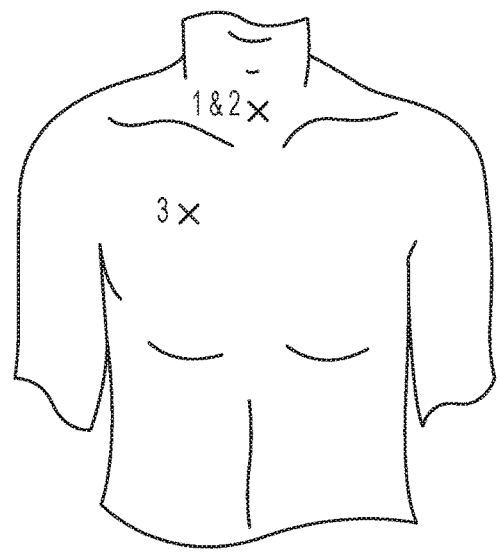
FIGS. 2A and 2B show entry sites for a percutaneous approaches to the mitral valve according to an exemplary embodiment. An 'x' marks approximate entry points: Suprasternal notch for Transcervical (Suprasternal) approach (1) and Pre-Tracheal Approach (2), right anterior chest for example in the second or third intercostal space anteriorly for the Right Anterior Approach (3) and entry site on the back to the right of the midline for the Posterior Approach (4).
Figure 2B:
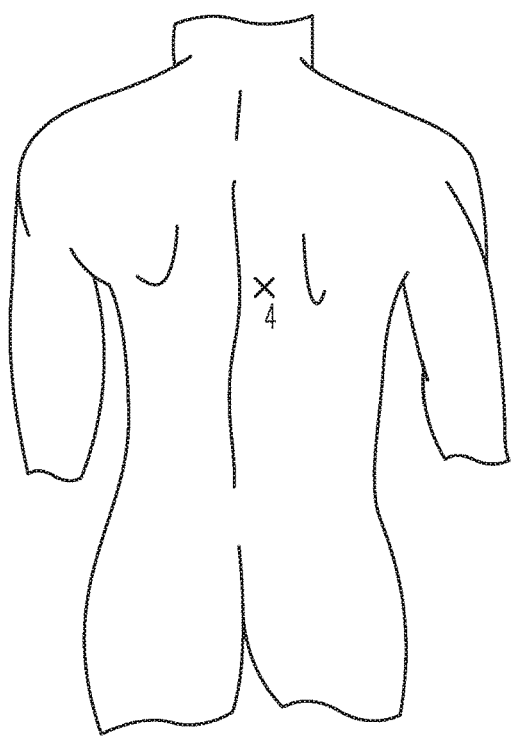
Figure 3A:
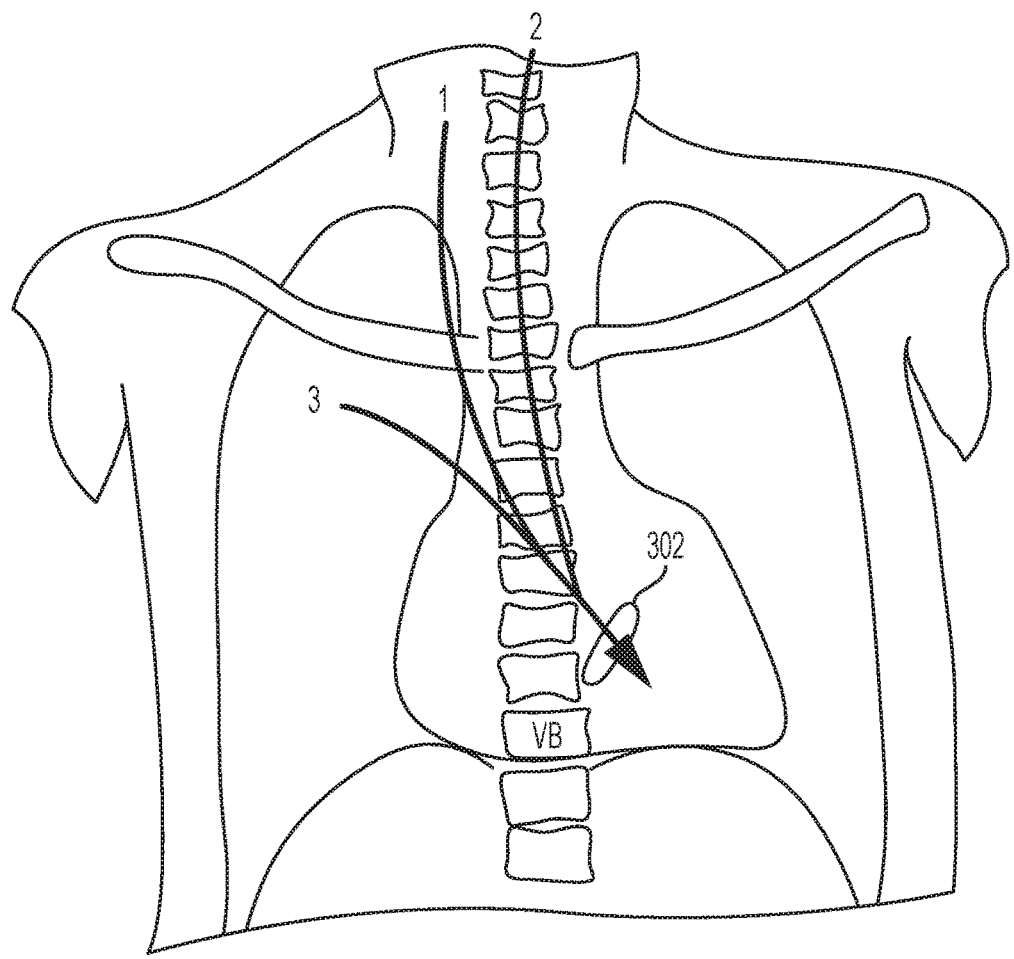
FIG. 3A show percutaneous mitral valve approaches according to an exemplary embodiment: the Transcervical (Suprasternal) Approach (1), the Pre-Tracheal Approach (2) and the Right Anterior Approach (3), on fluoroscopy with the X-ray tube positioned to provide a posteroanterior projection.
Figure 3B:
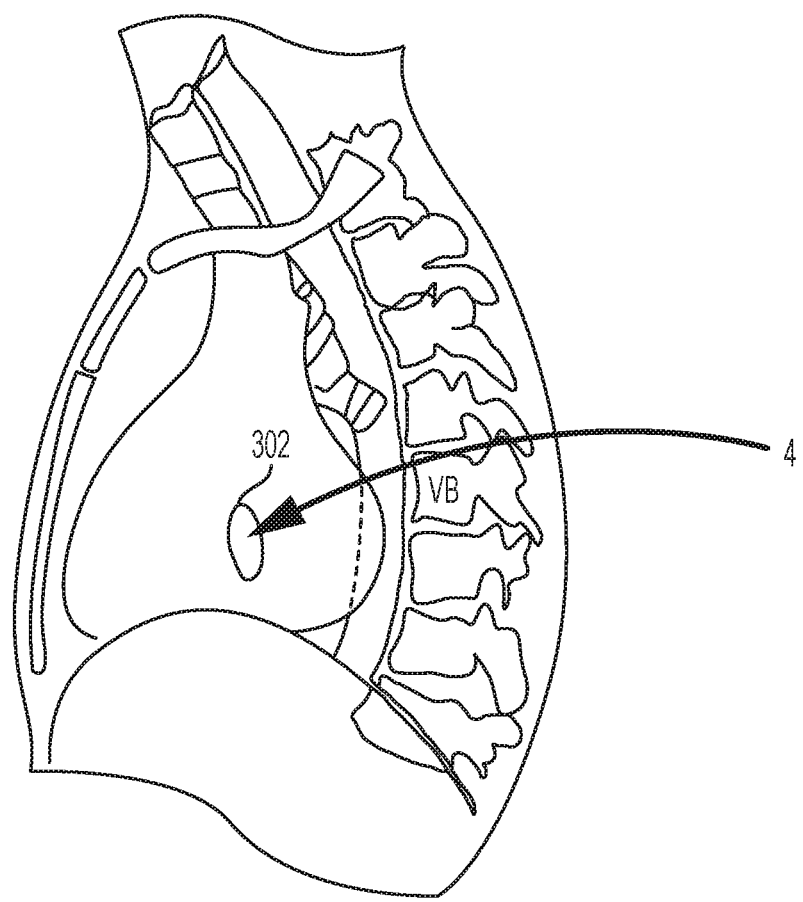
FIG. 3B shows a Posterior Approach (4) to the mitral valve on fluoroscopy with the X-ray tube positioned to provide a lateral projection according to an exemplary embodiment.

FIGS. 2A and 2B give a general overview of the entry points for approaches 1-4. FIGS. 3A and 3B show the approaches 1-4 superimposed upon skeletal structures likely to be seen, for example, on fluoroscopy. The oval 302 indicates a position of the mitral annulus which may or may not be visualized on fluoroscopy depending on the presence of calcification or previous mitral valve intervention. Arrows depict the general direction of the approaches 1-4. FIG. 3A shows the Transcervical (Suprasternal) Approach (1), the Pre-Tracheal Approach (2) and the Right Anterior Approach (3) on fluoroscopy with the X-ray tube positioned to provide a posteroanterior projection. FIG. 3B shows the Posterior Approach (4) on fluoroscopy with the X-ray tube positioned to provide a lateral projection.

Modes of carrying out mitral valve intervention using the approaches 1-4 are explained below:

Transcervical (Suprasternal) Approach

In a typical embodiment, the skin of the neck above the suprasternal notch is incised for percutaneous entry. The catheter is then advanced inferiorly under the sternal notch into the mediastinum. In various embodiments, the sternum is elevated with a retractor to enhance access, with or without the assistance of illumination.

In various embodiments, Catheter passes the innominate (left brachiocephalic) vein and, in various embodiments, the catheter is directed either anterior or posterior to the innominate vein.

Next, in a typical embodiment, the catheter is advanced towards a roof of the left atrium and the catheter is advanced lateral to the brachiocephalic artery.

In a typical embodiment, the pericardium is then penetrated and the catheter is advanced between the aorta, the superior vena cava and the right pulmonary artery. In a typical embodiment, the catheter is passed in such a way as to separate anatomical structures and create a space or passageway between anatomical structures that would otherwise lie in close apposition. In various embodiments, other means may be used to separate anatomical structures as will be discussed hereinbelow under CLOSURE.

In a typical embodiment, the catheter next passes anterior to the right pulmonary artery. The catheter passes lateral or posterolateral to the ascending aorta.

In various embodiments, navigation of the catheter around important vascular structures, may be directed by one or more or the following imaging methods, with or without suitable contrast agent(s): X-ray (fluoroscopy), computed tomography (CT), magnetic resonance imaging (MRI) or echocardiography, either transesophageal echocardiography, TEE, transthoracic echocardiography, TTE or by inserting the echo probe into a local anatomical structure such as jugular vein and then into the superior vena cava, intravascular echocardiography. A suitably protected echo probe may also be passed along the passage way in parallel with the catheter or inside the catheter to aid navigation.

In various embodiments, additional catheters may be introduced to facilitate visualisation of adjacent anatomical structures. For example, a second catheter may be placed in the right or left jugular vein and contrast injected to outline the position of the innominate (left brachiocephalic) vein and other venous structures such as the superior vena cave and right atrium.

Alternatively, a third catheter may be passed from the femoral or other suitable artery into aorta and through the aortic valve into the left ventricle and contrast injected so as to show the outline of the left atrium and/or the position of the aorta. The mitral valve regurgitation is likely to be present in subjects with mitral valve disease hence injection into the left ventricle will result in contrast entering both left atrium and ascending aorta, outlining both to aid navigation or confirm the position of the catheter in relation to these structures.

In various embodiments, additional catheters may be introduced into any of the chambers of the heart or blood vessels to aid navigation. Alternatively, a retractor may be introduced under the sternum and the sternum elevated to allow the catheter to be passed under direct vision or with the aid of a viewing device such as an endoscope. Further, in a typical embodiment, the pericardium is opened utilizing scissors positioned between the aorta and the superior vena cava; however, in other embodiments, other instruments could be utilized to open the pericardium.

In various embodiments, direct visualisation for safe passage of the catheter is improved by the use of one or more lights located on the retractor. In various embodiments, the catheter may be advanced under visualisation through use of a rigid or flexible endoscope, introduced through the same incision with the image preferably displayed upon a screen directly above the incision for ease of use. In various embodiments, the endoscope is either passed through a central lumen of the catheter or passed along a similar course as that described for the catheter.

In various embodiments, the catheter is attached to the left atrium by some means or positioned adjacent to the wall so as that needle means or a trocar may be passed through the first catheter into the left atrium thus creating a conduit or access route from outer surface of the skin to the inside of the left atrium. Alternatively, the catheter may be advanced into the left atrium itself to provide such access route. In various embodiments, devices are passed along the created access route to perform interventions on, for example, the mitral valve for mitral valve repair or replacement or to perform interventions on any other intracardiac structure or pathology.

In a typical embodiment, closure devices are directed to the site of opening in the left atrium by passage along the guide wire or inside the lumen of the catheter. By such means the opening in the left atrium may be closed out of the line of sight. If closure is unsuccessful by this means then greater exposure can be obtained by one or more of the following additional steps: In a typical embodiment, closure may be effected by use of a suture such as, for example, a purse string suture. The purse string suture is placed in the left atrium prior to introduction of the catheter with the retractor and guide wire into the left atrium within the boundaries of the previously-placed suture. After the withdrawal of all guide wires and catheters, the suture is tied using a long instrument such as, for example, a knot pusher. In other embodiments, any appropriate method of securing a purse string suture may be employed.

In various embodiments, an instrument is used to retract or push the aorta to the left to improve exposure to the roof of the left atrium. In various embodiments, suction catheter is required to be passed along a similar route to enhance visualisation if there is bleeding from the opening in the atrium.

In various embodiments, retraction of the aorta is made easier by temporarily reducing the cardiac output by rapid ventricular pacing. Alternatively, cardiopulmonary bypass may be established and the flow temporarily reduced to facilitate retraction of the aorta. If these measures are still insufficient to obtain adequate access for closure of the site of entry into the left atrium then the aorta may be cross clamped and cardioplegia instilled into the aortic root to arrest the heart thereby rendering the aorta flaccid and easily manipulated. Closure is then obtained by surgical means for example by suturing. After successful closure, the circulation is restored to the heart by release of the aortic cross clamp and after a period of recovery the heart may be weaned from cardiopulmonary bypass in the normal manner.

In various embodiments, these same techniques may of course be used to improve exposure of the atrium to allow precise localisation of the site of penetration of the catheter, trocar, needle or guide wire through the wall of the left atrium. In various embodiments, haemostatic agents or closure devices to also be directed to the puncture site with the catheter. In various embodiments, a drain may be directed to the site by the guide wire or catheter and left in place at the end of the procedure to prevent accumulation of fluid in the pericardial space.

Figure 4A:
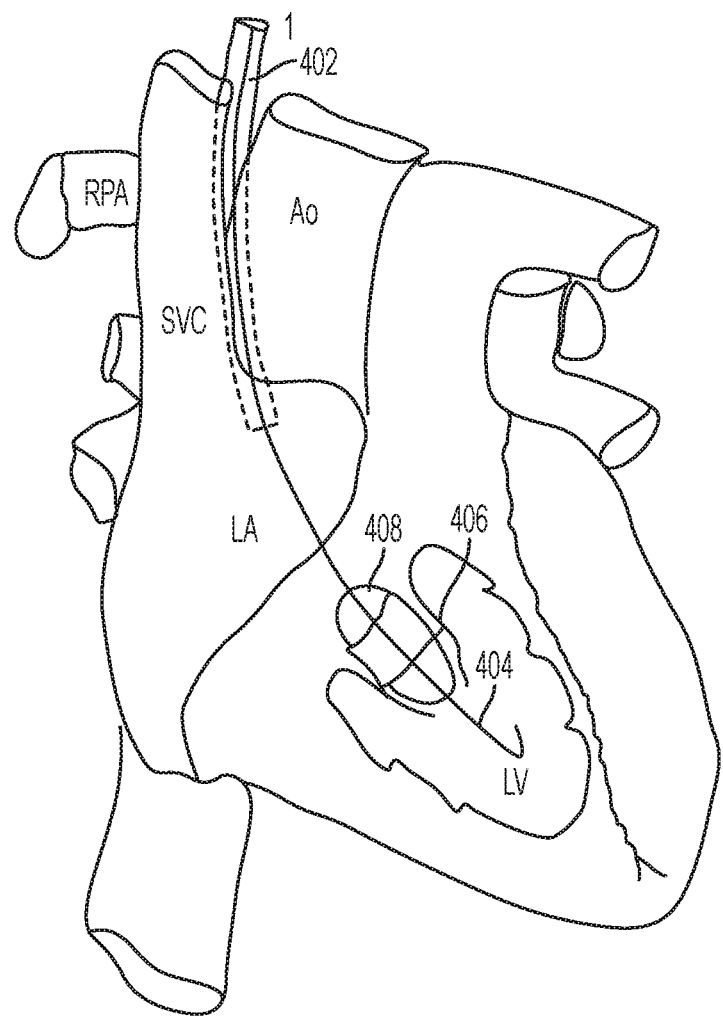
FIG. 4A is an anatomical view of an anterior aspect of the heart showing the relationship of a catheter to the heart and great vessels in a Transcervical (Suprasternal) Approach according to an exemplary embodiment.

FIG. 4A is an anatomical view of an anterior aspect of the heart showing the relationship of the catheter to the heart and great vessels in the Transcervical (Suprasternal) Approach (1). The tip of the catheter 402 is positioned above the roof of the left atrium (LA) but is obscured from view behind the ascending aorta ($A_o$) and the superior vena cava (SVC) as it enters the left atrium (LA).

Figure 4B:
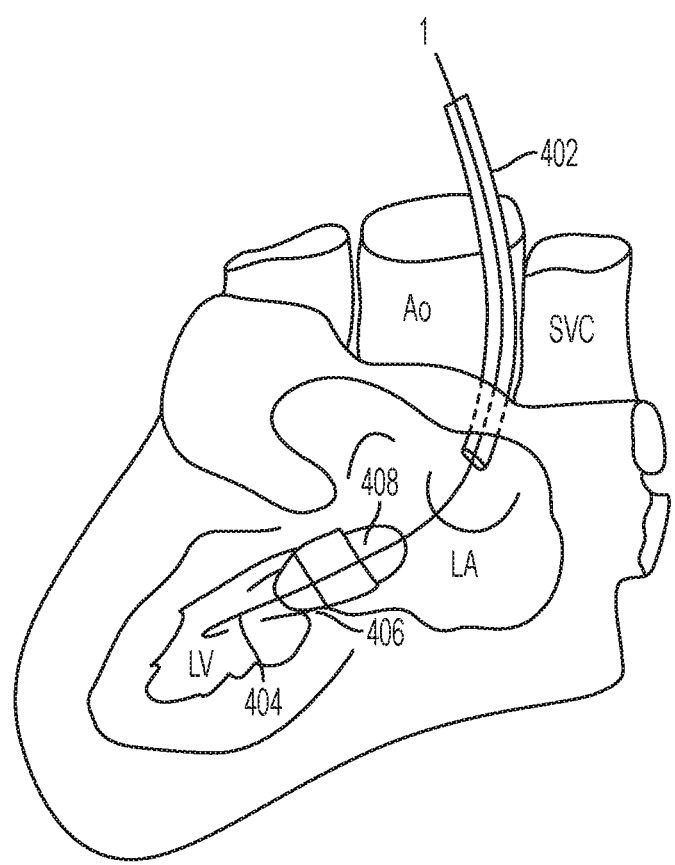
FIG. 4B is an anatomical view of a posterior aspect of the heart showing the relationship of the catheter to the heart and great vessels in the Transcervical (Suprasternal) Approach according to an exemplary embodiment.

FIG. 4B is an anatomical view of a posterior aspect of the heart showing the relationship of the catheter 402 to the heart and great vessels in the Transcervical (Suprasternal) Approach (1). The figure shows the tip of the catheter positioned just outside of the left atrium (LA) and a guide wire 404 passing through the roof of the left atrium (LA) into the left atrial chamber and then through the mitral valve orifice 406 into the left ventricle (LV). A transcatheter heart valve device 408 is shown mounted on the guide wire 404 in the mitral valve orifice 406, for illustrative purposes, as an example of intervention that can be performed on the mitral valve through this access route.

Figure 5A:
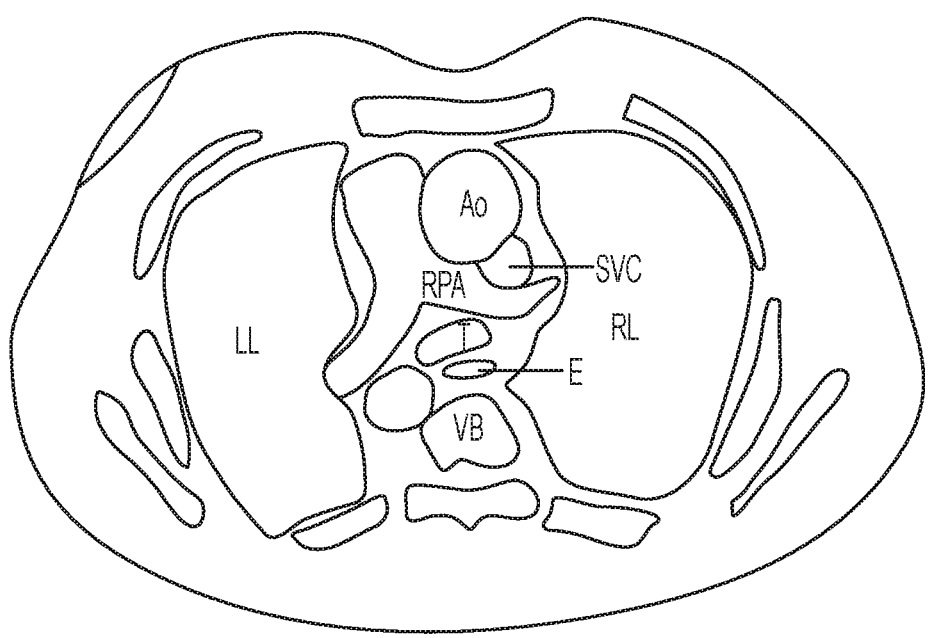
FIG. 5A is a transverse section through the chest at the level of the pulmonary arteries to show the disposition of anatomical structures according to an exemplary embodiment. Note that the ascending aorta (Ao), superior vena cava (SVC) and right pulmonary artery (RPA) lie in close apposition. Other structures shown are right lung (RL), left lung (LL), trachea (T), esophagus (E), vertebral body (VB).

FIG. 5A is a transverse section through the chest at the level of the pulmonary arteries to show the disposition of anatomical structures. Note that the ascending aorta (Ao), superior vena cava (SVC) and right pulmonary artery (RPA) lie in close apposition. Other structures shown are right lung (RL), left lung (LL), trachea (T), esophagus (E), vertebral body (VB).

Figure 5B:
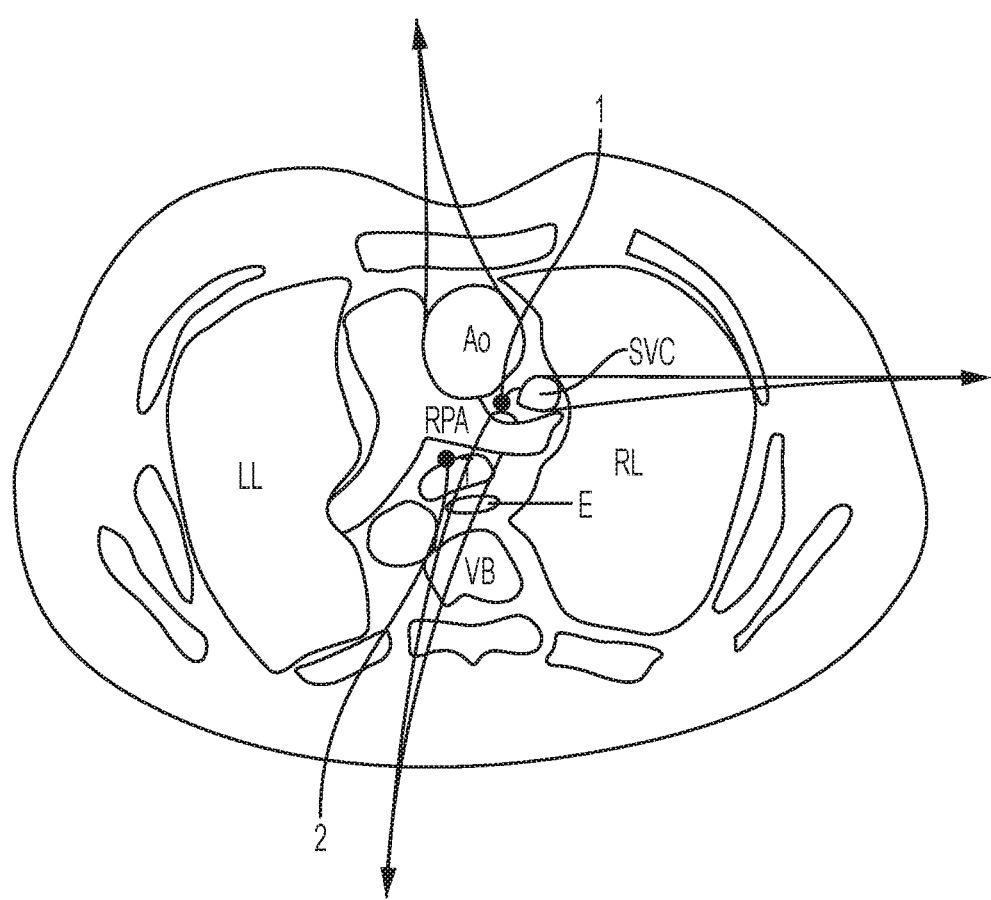
FIG. 5B is the same view as FIG. 5A with the superior vena cava (SVC), the right pulmonary artery (RPA) and the ascending aorta (Ao) retracted with slings in the direction shown by the arrows to show where a catheter would pass between these structures in the Transcervical (Suprasternal) Approach (1) and Pre-Tracheal Approach (2), according to two exemplary embodiments.

FIG. 5B is the view as FIG. 5A with the superior vena cava (SVC), right pulmonary artery (RPA), and ascending aorta (Ao) retracted with slings in the direction shown by the arrows to show where the catheter 402 would pass between these structures in the Transcervical (Suprasternal) Approach (1), if they were pushed or pulled apart. It is not part of the method to retract these structures with slings, rather the method is to push them aside by the passage of a blunt instrument or catheter and/or dilator(s). Note also the close proximity of the right pulmonary artery (RPA) to the anterior surface of the trachea (T). In the Pre-Tracheal Approach (2), the catheter must pass behind the right pulmonary artery.

Figure 6:
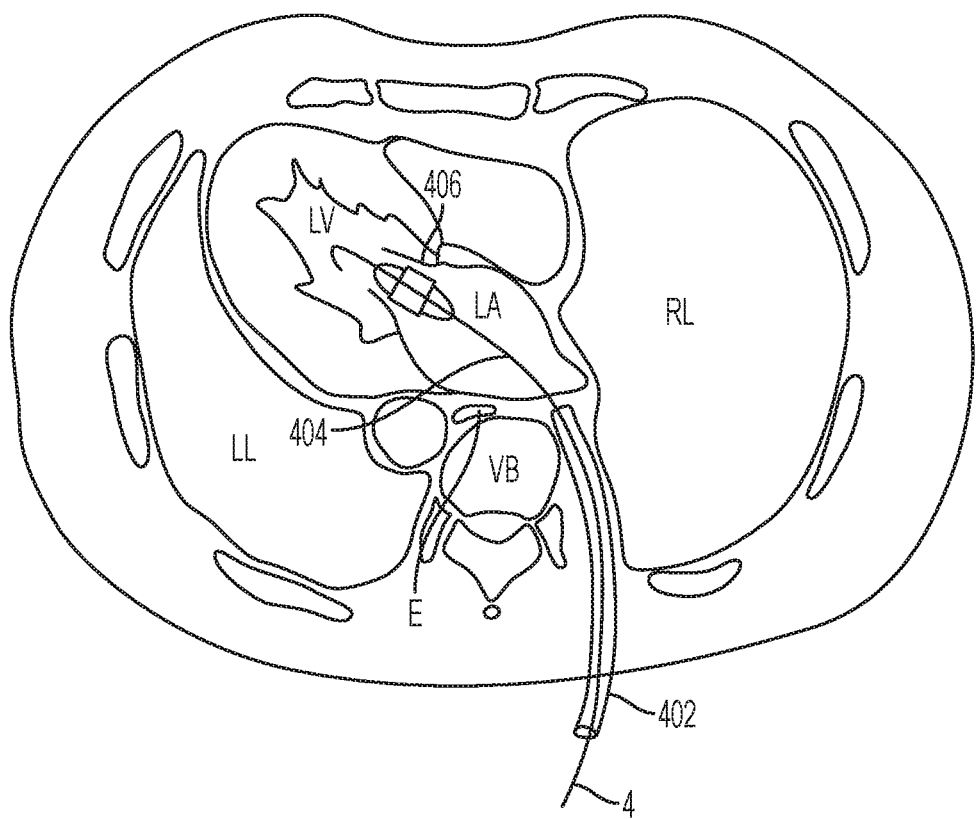
FIG. 6 is a transverse section through the body at the level of the left atrium to show passage of a catheter by the Posterior Approach (4) according to an exemplary embodiment.

FIG. 6 is a transverse section through the body at the level of the left atrium to show passage of the catheter 402 by the Posterior Approach (4). The catheter 402 approaches the left atrium (LA) by passing between the right lung (RL) and the vertebral body (VB). FIG. 6 shows the tip of the catheter 402 positioned just outside of the left atrium (LA) and the guide wire 404 passing through the wall of the left atrium (LA) into the left atrial chamber and then through the mitral valve orifice 406 into the left ventricle (LV). Note the position of the esophagus (E) in front of the vertebral body which must be pushed to one side by the catheter 402 to avoid injury.

Figure 7:
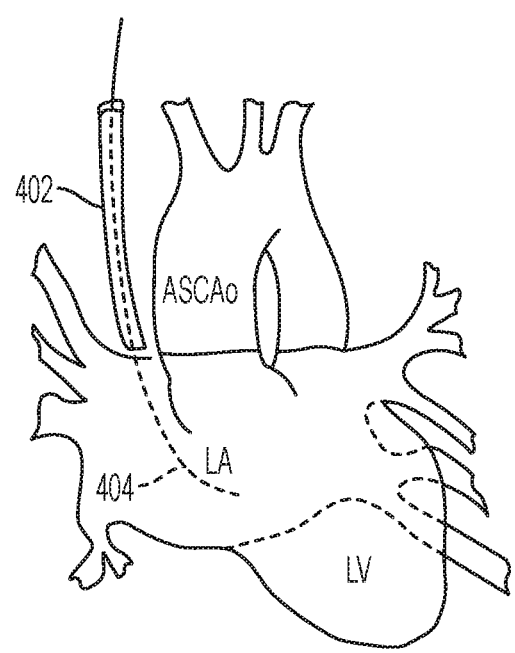
FIG. 7 is an angiogram of left heart structures: the left atrium (LA), the left ventricle (LV) and the ascending aorta (Ao) viewed from the anterior aspect to illustrate the position of the left heart structures in general and left atrium in particular, with right heart structures (superior vena cava, right atrium and right ventricle) effectively removed from the view.

FIG. 7 is an angiogram of left heart structures: the left atrium (LA), the left ventricle (LV) and the ascending aorta (ASC Ao) viewed from an anterior aspect to illustrate the position of the left heart structures in general and left atrium in particular, with right heart structures (superior vena cava, right atrium and right ventricle) effectively removed from the view. An angiogram may be used to guide the operator in passing the catheter 402 towards the left atrium (LA). Position of the catheter 402 with its tip positioned immediately outside of the roof of the left atrium (LA) using the transcervical (suprasternal) approach (1) is shown; the guide wire 404 is shown entering the left atrium (LA) and passing through the mitral valve in broken line. Radio opaque markings on the catheter (not shown) would be seen in this view Pre-Tracheal Approach In a typical embodiment, skin above the suprasternal notch is incised in the midline for percutaneous entry. In a typical embodiment, dissection is undertaken to expose tissues directly in front of the trachea. The catheter is introduced into the pretracheal plane.

In a typical embodiment, the catheter is advanced inferiorly over the anterior surface of the trachea to level of carina. In various embodiments, progress may be followed on fluoroscopy which outlines the trachea nicely or by any of the other imaging methods listed above. Alternatively the skin incision may be enlarged so that progress may be followed by direct vision by the surgeon looking down the catheter or the passage may be created with a mediastinoscope in advance of passing the catheter.

In a typical embodiment, the pericardium is penetrated and the catheter is advanced beyond the carina so that a tip of the catheter is positioned just outside of the left atrium thus creating thus creating a conduit or access route from outer surface of the skin to the left atrium. Alternatively, catheter may be advanced into the left atrium itself to provide such access route.

In various embodiments, devices may be passed along the created access route to perform interventions on the mitral valve for mitral valve repair or replacement or to perform interventions on any other intracardiac structure or pathology. In various embodiments, closure devices may be directed to the site of puncture in the left atrial wall by the new conduit. In various embodiments, the conduit also permits hemostatic agents or devices to be directed to the puncture site.

In various embodiments, passage can be optionally widened using dilators. In various embodiments, catheter means may be optionally used to direct the tip of the catheter.

In various embodiments, navigation of the catheter around these important vascular structures, is directed by one or more or the following image methods, with or without suitable contrast agent(s): X-ray (fluoroscopy), computed tomography (CT), magnetic resonance imaging (MRI) or echocardiography, either transesophageal echocardiography, TEE, transthoracic echocardiography, TTE or by inserting the echo probe into a local anatomical structure such as jugular vein and then into the superior vena cava, intravascular echocardiography. In various embodiments, a suitably protected echo probe is also be passed along the passage way or inside the catheter to aid navigation.

In various embodiments, additional catheters may be introduced to facilitate visualisation of adjacent anatomical structures. For example, a pulmonary artery catheter may be passed from the right jugular vein into the superior vena cava then into the right atrium then right ventricle then into the main pulmonary artery. Catheter is preferably advanced into the right pulmonary artery to show approximate position of right pulmonary artery (RPA) which is a closely related anatomical structure in this route.

In various embodiments, a drain is left in place temporarily after removal of the catheter in order to prevent accumulation of blood while the entry point into the left atrium begins to heal and becomes haemostatic.

Right Anterior Approach

In a typical embodiment, skin over, for example, the second or third intercostal space to the right of the midline is incised for percutaneous access. In various embodiments, the chest wall is elevated or spread with a rib spreading retractor or a soft tissue retractor to enhance access, with or without the assistance of illumination. In various embodiments, the rib spreading retractor is equipped with one or more lights to provide illumination to the field and aid safe passage of the catheter.

In a typical embodiment, the pericardium is penetrated. The catheter is advanced towards left atrium by passing between ascending aorta (Ao), superior vena cava (SVC) and right pulmonary artery (RPA).

In various embodiments, navigation of the catheter around these important vascular structures, is directed by one or more or the following image methods, with or without suitable contrast agent(s): X-ray (fluoroscopy), computed tomography (CT), magnetic resonance imaging (MRI) or echocardiography, either transesophageal echocardiography, TEE, transthoracic echocardiography, TTE or by inserting the echo probe into a local anatomical structure such as jugular vein and then into the superior vena cava, intravascular echocardiography. In various embodiments, a suitably protected echo probe is also be passed along the passage way or inside the catheter to aid navigation.

In various embodiments, an imaging modality such as echocardiography may be used to identify the position of the ipsilateral internal thoracic artery and vein which are at risk during this approach. In various embodiments, additional catheters are introduced to facilitate visualisation of adjacent anatomical structures, For example, a second catheter may be placed in the left jugular vein and contrast injected to outline the position of the superior vena cava (SVC).

Alternatively, a third catheter may be passed from the femoral or other suitable artery into aorta and through the aortic valve into the left ventricle and contrast injected so as to show the outline of the left atrium and/or the position of the aorta. The mitral valve regurgitation is likely to be present in subjects with mitral valve disease hence injection into the left ventricle will result in contrast entering both left atrium and ascending aorta. In various embodiments, additional catheters may be introduced into any of the chambers of the heart or blood vessels to aid navigation.

In various embodiments, the catheter is attached to the left atrium by some means or positioned adjacent to the wall so as that trocar or needle means may be passed through the first catheter into the left atrium thus creating a new conduit or access route from outer surface of the skin to the inside of the left atrium. Alternatively, the catheter may be advanced into the left atrium itself to provide such access route.

In various embodiments, devices are passed along the created access route to perform interventions on the mitral valve for mitral valve repair or replacement or to perform interventions on any other intracardiac structure. In various embodiments, closure devices are directed to the site of puncture in the left atrial wall by the new conduit. The conduit also permits hemostatic agents or devices to be directed to the puncture site. In various embodiments, a drain may optionally be left in place temporarily after removal of the catheter in order to prevent accumulation of blood whilst entry point into the left atrium begins to heal and becomes haemostatic.

Posterior Approach

In a typical embodiment, skin over the back to the right of the midline is incised for percutaneous access. The catheter is advanced into the space between the pleura covering the right lung and the vertebral body so that its tip is positioned just outside of the left atrium. In various embodiments, this space can optionally be distended with injection of liquid or gas to displace tissues.

In various embodiments, the catheter may be advanced so that a tip of the catheter becomes attached to the left atrium by some means or positioned adjacent to the wall so as that trocar or needle means may be passed through the first catheter into the left atrium thus creating a new conduit or access route from outer surface of the skin to the inside of the left atrium. In various embodiments, the catheter may alternatively be advanced into the left atrium itself to provide such access route.

In various embodiments, devices are passed along the newly created access route to perform interventions on the mitral valve for mitral valve repair or replacement or to perform interventions on any other intracardiac structure. In various embodiments, closure devices may be directed to the site of puncture in the left atrial wall by the new conduit. The conduit also permits haemostatic agents or devices to be directed to the puncture site. In various embodiments, the patient may be placed prone for the procedure or other position to provide favourable working access for the operator and/or displacement of anatomical structures by gravity.

In various embodiments, navigation of the catheter around important vascular and non vascular structures, may be directed by one or more or the following image methods, with or without suitable contrast agent(s): X-ray (fluoroscopy), computed tomography (CT), magnetic resonance imaging (MRI) or echocardiography, either transoesophageal echocardiography, TEE, transthoracic echocardiography, TTE or by inserting the echo probe into a local anatomical structure such as jugular vein and then into the superior vena cava, intravascular echocardiography. In various embodiments, a suitably protected echo probe may also be passed along the passage way or inside the catheter to aid navigation.

In various embodiments, additional catheters are introduced to facilitate visualisation of adjacent anatomical structures. For example the position of esophagus may be marked by placing a catheter or bougie within its lumen and/or by injection of contrast into its lumen (or contrast swallow if the patient is conscious). A transesophageal echo probe placed within its lumen may serve this purpose of depicting the position of the oesophagus which is otherwise at risk during this approach. In various embodiments, a drain may optionally be left in place temporarily after removal of the catheter in order to prevent accumulation of blood whilst entry point into the left atrium begins to heal and becomes haemostatic.

Unlike the Trans Apical and Femoral Venous approaches, the percutaneous approaches 1-4 devised by the present inventors satisfy all six of the preferred criteria as follows:

1. It DOES follow a smooth curve from point of entry to the mitral valve.

2. It DOES enter the circulation through a low pressure chamber, the left atrium.

3. It DOES approach the mitral valve in an antegrade direction.

4. It DOES provide a short route to the mitral valve—it is much shorter than from the femoral vein.

5. It DOES have point of entry from a clean area. The neck, back and even anterior chest are clean areas, not typically colonised by organisms other than normal commensals.

6. It DOES provide access without causing undue pain or discomfort. Wounds in the neck area do not move with respiration or ambulation so tend to be less painful. likewise there is little movement in the skin over the back during normal respiration. They may also be analgised effectively by instillation of local anaesthesia at the time of the procedure and with simple over the counter analgesics such as Paracetamol (Acetaminophen) over the ensuing few days, if required.

In summary, the new approach satisfies all of the six preferred criteria, outlined above. It therefore overcomes problems identified with each of the existing approaches. The essence of the new approach is to create a new extra-anatomical route, in effect a conduit between the skin's surface and the left atrium. Although it is envisaged that a catheter be passed along this route, and positioned immediately outside of the left atrium, it would be equally possible to connect the conduit to the left atrium or even to enter the left atrium with the conduit.

Various surgical devices would facilitate surgery via these new surgical approaches. These are explained below.

Catheter Holding Device

It is normal practice for the catheter to be held by the operator or an assistant so that the operator may use his or her hands to maintain the position of the catheter whilst devices are passed through the catheter or over the guide wire. However, this exposes the operator or assistant's hands to harmful irradiation as the catheter is in close proximity to the X-ray field; it also ties up the hands of the operator or his assistant which might otherwise be used to guide the device along the guide wire and for operation of device deployment mechanism(s). Secure fixation of the catheter to a support either to the skin itself or to a stationary item of the surgical apparatus, for example a retractor, frees up the hands of the operator and the assistant and takes their hands away from the harmful X-ray field. Secure fixation also means the catheter is less likely to move during the above operations than if held by the operator or the operator's assistant thus allowing more accurate placement and deployment of intravascular devices. It would also provide a more stable platform for robotic manipulation of the catheter allowing device delivery, guide wire and/or catheter manipulation to be performed at a distance or potentially even remotely from the protection of a control with the use of a robotic manipulator, ensuring the safety of the operator. Exposure of the operator to irradiation during fluoroscopic procedures is a well recognized problem in the field and source of considerable anxiety amongst staff, especially staff of child bearing age.

Figure 9:
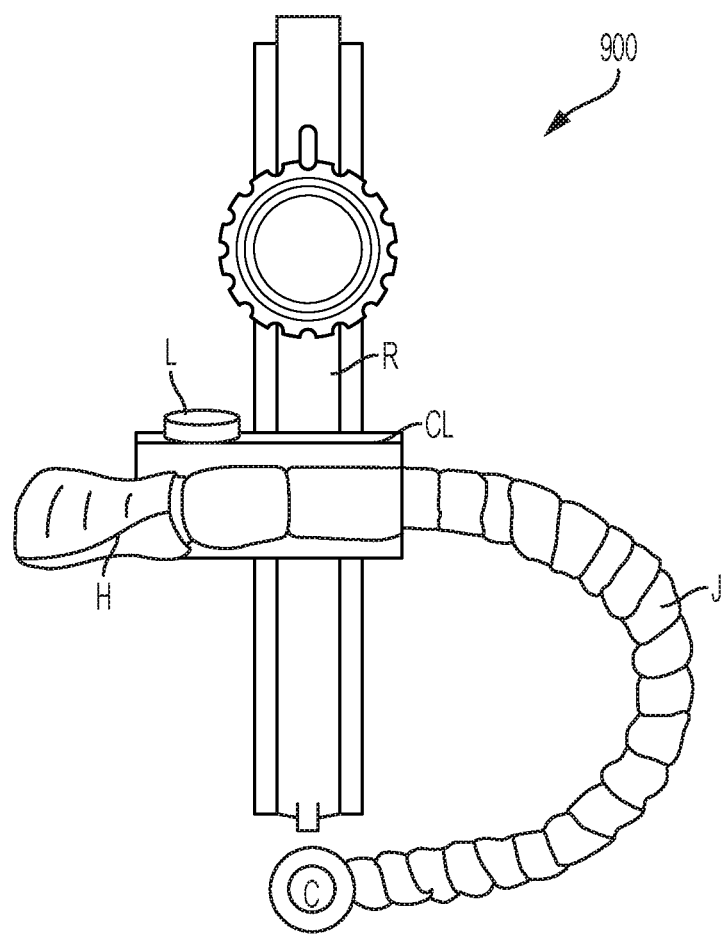
FIG. 9 Example of a retractor (R) with a supporting device according to an exemplary embodiment.

FIG. 9 shows an example of a catheter positioning device devised by the present inventors. The device 900 comprises a series of articulated joints (J); at one end a clamp (CL) that connects with a retractor and is locked to the retractor by locking switch (L); at the other end a collar that attaches securely around the catheter (C); a handle (H) may be turned so that in one direction articulated joints are loose, allowing the supporting device to be manipulated into an optimal position and when turned in the opposite direction the articulated joints become solid so that the catheter (C) is held securely in space.

Replacement Heart Valve Prosthesis

The transcatheter heart valve prosthesis is oriented on the delivery catheter so that the inflow portion of the valve faces the operator when used with this method. When such a heart valve prosthesis is inserted by this method the orientation of the valve in the deployed state will be such that the valve allows blood to pass from the left atrium to the left ventricle but prevents or substantially prevents blood from passing from the left ventricle to the left atrium during systole.

Figure 10:
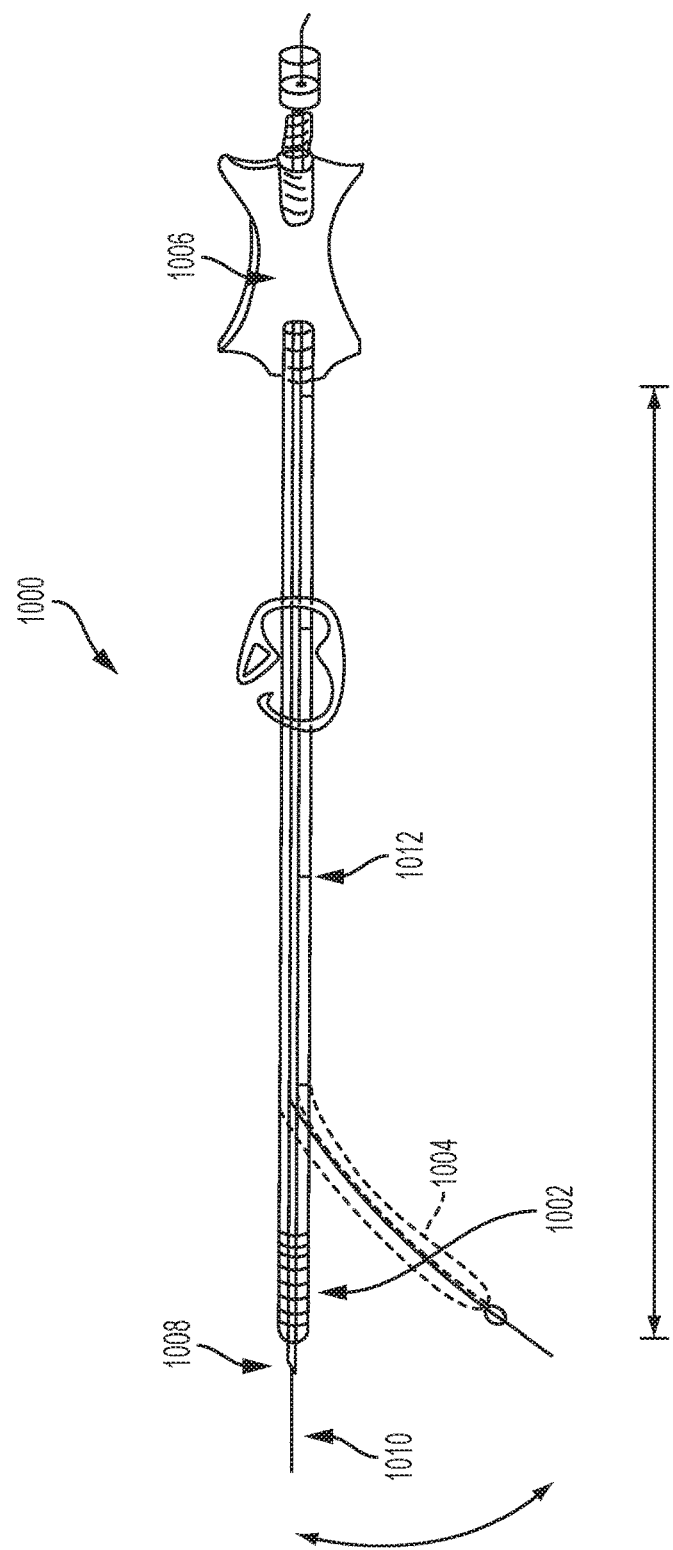
FIG. 10 is an example of a catheter for providing access to the left atrium to perform percutaneous or transcatheter intervention on the mitral valve of the heart according to an exemplary embodiment.

Hooks or barbs on the stent or frame of such devices are oriented to prevent valve displacement towards the left atrium from the left ventricle. Thereby avoid risk of valve being displaced into the left atrium. The transcatheter heart valve prosthesis is mounted on the delivery catheter so that such hooks or barbs face backwards i.e. towards the operator for the valve to be implanted by this method. In a typical embodiment, the valve may be preloaded in the correct orientation on a suitable catheter for use by this method Catheter System Example of a catheter that may be used in this method is shown in FIG. 10.

In a typical embodiment, the catheter 1000 includes a blunt tip 1002 so that the catheter can be advanced between major blood vessels without the likelihood of penetrating them inadvertently. In various embodiments, the blunt tip 1002 may be tapered to facilitate passage through the tissues including loose areolar tissue, the pericardium, fibrous adhesions within the pericardium and the left atrial wall itself.

In various embodiments, the catheter 1000 may be straight or exhibit a smooth curvature 1004 at a distal end (see dotted lines) to direct passage towards the left atrium. The curvature 1004 may be created at time of manufacture or else the catheter and trocar may be made from a malleable material so that the catheter 1000 can be bent to the desired curvature by the physician user.

Alternatively the tip of the catheter 1000 may be steerable. That is, the tip of the catheter 1000 may be capable of bending at the tip in at least one plane by a control mechanism on the handle (not shown) such that in one position the catheter 1000 is straight and in other positions the catheter 1000 is curved. The curvature 1004 being modified so as to steer the catheter towards the left atrium.

In various embodiments, the catheter 1000 includes a handle 1006 to facilitate manipulation of the catheter and aid in orientation of the curvature 1004 at the tip. In various embodiments, the handle 1006 may have grips for two fingers and thumb to aid precise manipulation of the catheter 1000 by the physician operator.

In various embodiments, the catheter 1000 may have graduated markings 1012 so that the user knows how far inside the patient the catheter 1000 has advanced. Such markings may be radio opaque or else easily visible by ultrasound to aid navigation of the catheter 1000 by, for example, imaging.

In various embodiments, the catheter 1000 may have a central lumen capable of accommodating a trocar 1008 or needle means. The trocar or needle means 1008 may have a sharp or beveled tip for penetrating pericardium or wall of left atrium or fibrous tissue caused by previous surgery or pericardial disease. In a typical embodiment, the trocar or needle means 1008 is capable of being withdrawn or advanced within the catheter 1000 manually by the user. Alternatively, the catheter 1000 may incorporate spring mechanism such that in the resting state the trocar or needle means 1008 is retracted inside the blunt tip 1002 of the catheter 1000 and the user is required to press against a spring mechanism to advance the trocar 1008 so that it protrudes beyond the blunt tip 1002 of the catheter 1000. Such position is desirable for advancing the device through fibrous structures such as the pericardium, the left atrial wall or through fibrous adhesions. In various embodiments, the trocar or needle means 1008 may have a central lumen to accommodate a guide wire 1010.

In various embodiments, the trocar or needle means 1008 may have a cap that is be adapted to receive a syringe (not shown) or be fitted with a filter (not shown) so that entry into the left atrium is signified by a 'flash back' of red blood into the filter. Such filter may be exchangeable for a syringe or be removable so that a guide wire (shown) may be passed through the central lumen of the trocar.

In a typical embodiment, the minimum working length of the catheter 1000 and/or trocar or needle means 1008 must be sufficient for the blunt tip 1002 to reach to left atrium from the skin surface with the handle 1006 remaining outside of the body. Length of the catheter 1000 and/or trocar 1008 should not be so long as to be unwieldy and difficult to manipulate. An optimal length of between 15 cm and 52 cm is desired from the blunt tip 1002 of the catheter 1000 to the handle 1006 or portion of the catheter where guide wire 1010 is received (if no handle)

In various embodiments, the catheter 1000 is equipped with an external clip (shown) or internal valve mechanism (not shown) to prevent air from entering the left atrium which could potentially embolise within the circulation causing stroke, so called 'air embolus' when the trocar and/or guide wire is removed. In various embodiments, the catheter 1000 may incorporate an additional lumen (not shown) for connection to manometer line or blood sampling line or for installation of fluid to aid its passage In various embodiments, the catheter 1000 may be made from rigid or semi-rigid material so as to hold is shape. Alternatively, catheter 1000 may be flexible and derive its rigidity from the trocar or needle means 1008 contained within.

In various embodiments, the catheter 1000 or the trocar or needle means 1008 may be from radio-opaque material or have radio-opaque marking 1012 to facilitate imaging of device by the imaging methods outlined. Markings 1012 may have markings to convey information about distances from the tip or other physical landmarks or parts of the catheter system. In various embodiments, dilators are used (may be bent) with this method to facilitate passage of successively larger catheters such that s catheter of sufficient size is in place for delivery of a transcatheter heart valve prostheses.

A delivery catheter is used to deliver and deploy a transcatheter mitral valve prosthesis, mitral repair device, or other interventional device to a correct anatomical location such as, for example, a mitral valve annulus. The delivery catheter may be passed into the left atrium through the lumen of the catheter of FIG. 10 after removal of the trocar or else may be exchanged over the guide wire shown in FIG. 10.

Figure 12:
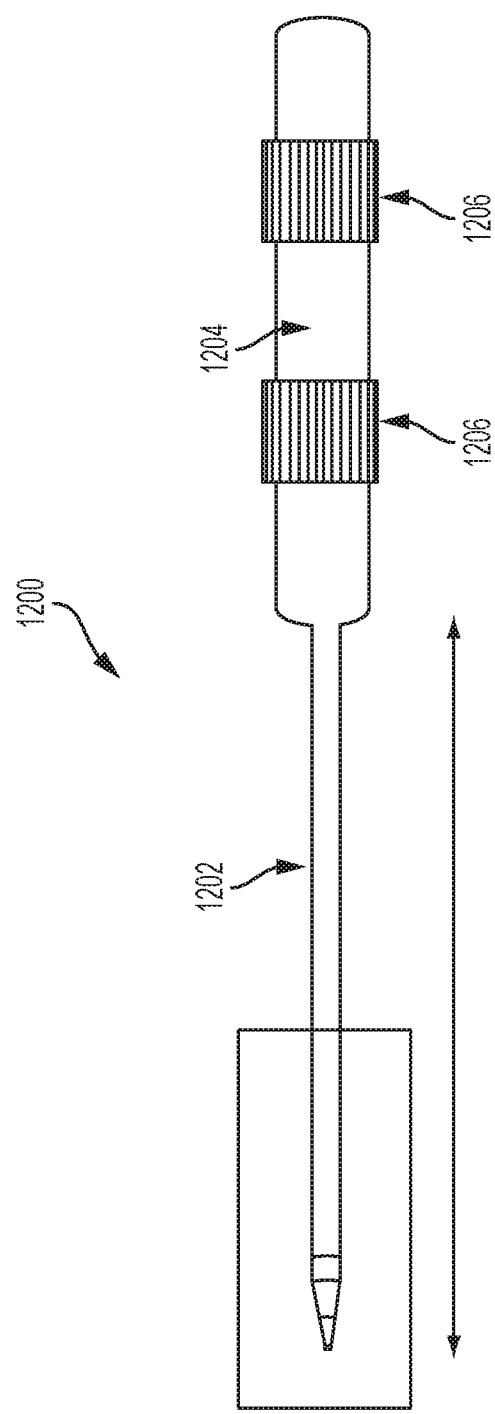
FIG. 12 is a plan view of a delivery catheter according to an exemplary embodiment.
Figure 13A:
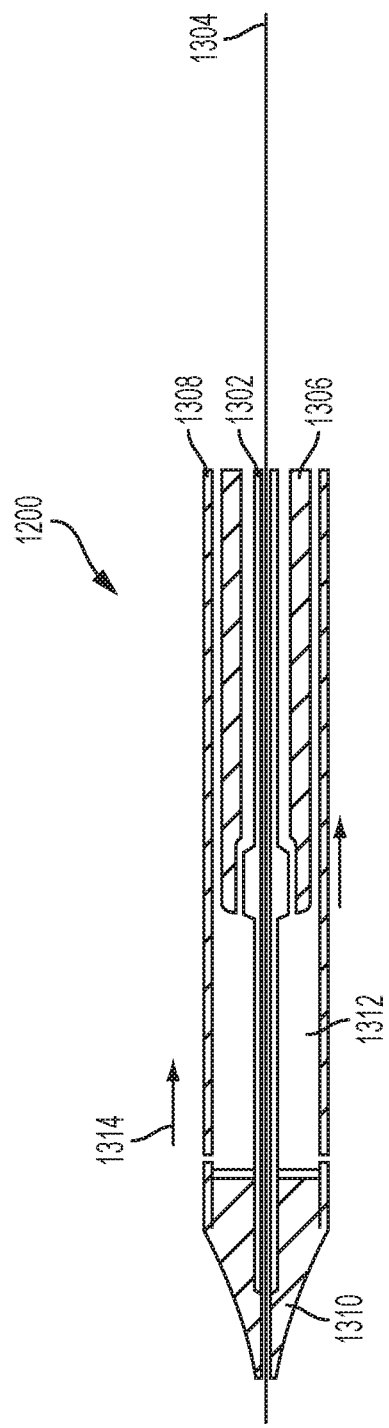
FIG. 13A is a cross-sectional view of a delivery catheter in a closed state according to an exemplary embodiment.
Figure 13B:
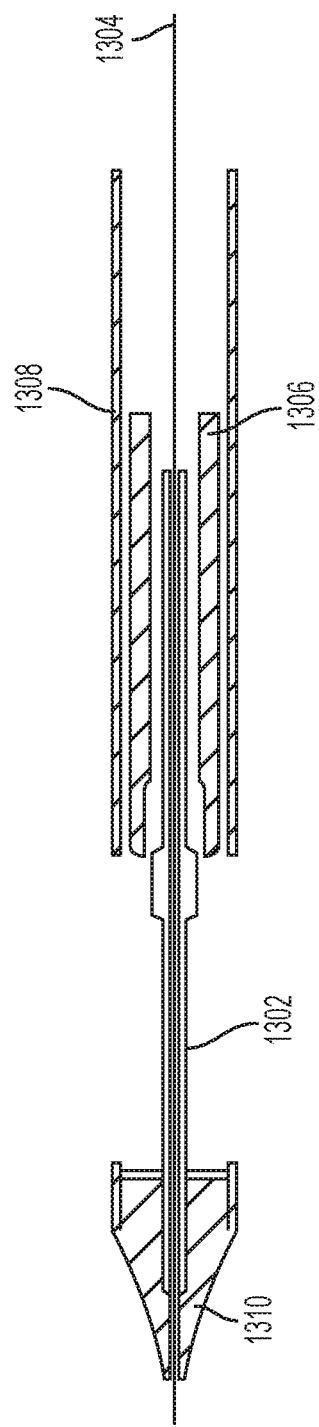
FIG. 13B is a cross sectional view of a delivery catheter in an open state according to an exemplary embodiment.

FIG. 12 shows a delivery catheter 1200 for use with this method that comprises a series of concentrically nested catheters. As shown in FIGS. 13A and 13B, the delivery catheter 1200 includes a first inner catheter 1302 that may optionally accept a guide wire 1304 through its central lumen and extends throughout the length of the delivery catheter 1200, a second hub catheter 1306 that is used to hold a valve on the inner catheter 1302 and a third outer catheter or sheath catheter 1308 that encircles the hub catheter 1306 and may be advanced distally so that the sheath catheter 1308 covers an entire length of the valve prosthesis and restrains the valve in a crimped state on the delivery catheter 1200 until the valve is ready to be deployed at a correct anatomical site. In various embodiments, additional catheters may be concentrically located to add rigidity and/or maintain haemostasis in the delivery catheter 1200 or further to advance a nose cone 1310 or unsheathe the valve in an opposite direction.

The delivery catheter 1200 comprises a shaft 1202 and a handle 1204. The handle 1204 provides a location for control mechanisms that move the catheters 1302, 1306, 1308 relative to one another. The mechanism for moving the catheters 1302, 1306, 1308 relative to one another typically include a thumb wheel 1206 mounted on the handle 1204 and mating with a threaded insert that is attached to the respective catheter which catheter is then advanced or retracted by turning the thumbwheel 1206. By way of example, two thumbwheels 1206 are illustrated in FIG. 12; however, in other embodiments, delivery catheters according to principles of the invention may incorporate more or fewer thumbwheels 1206 as dictated by design requirements. The control wheels 1206 control, for example, the outer sheath catheter 1308 and the hub catheter 1306.

In a typical embodiment, the distal tip of the delivery catheter 1200 includes a nose cone 1310 or atraumatic tip to prevent damage to the mitral valve or related anatomical structures as the delivery catheter 1200 is advanced into, for example, the left atrium through the mitral valve and onwards into the left ventricle. In various embodiments, the delivery catheter 1200 may be modified with additional catheters incorporated to advance or retract the nose cone 1310 or confer other functions on the delivery catheter 1200.

In the delivery catheter 1200 shown in FIGS. 13A and 13B the heart valve prosthesis (not shown) is retained between an inner surface of the outer sheath catheter 1308 and an outer surface of the inner catheter 1302. In addition, the valve is also held at one end between the inner catheter 1302 and hub catheter 1306. Once the valve is mounted onto the inner catheter 1302, the hub catheter 1306 is advanced over the mating features such that the mating features hold that end of the valve on the delivery catheter 1200. The sheath catheter 1308 is then advanced over the rest of the valve so that the valve is retained in the space 1312 shown in FIG. 13A.

Typically, features on the valve will cooperate with a reciprocal mating features on one of the catheters such as, for example, the inner catheter 1302 to ensure correct position of the valve on the delivery catheter 1200. An example of such a feature would be, for example, a tab or number of tabs on the valve that fit into an equal number of slots or mating features on the delivery catheter 1200. As such features are typically located at one end of the valve the process of mating these reciprocal parts provides a means for ensuring correct orientation of the valve on the delivery catheter 1200 for the desired direction of delivery, in this method antegrade delivery.

In various embodiments, the delivery catheter 1200 includes a steering wire (not shown) attached close to the tip of the delivery catheter 1200 and led along a length of the delivery catheter 1200 to a control wheel 1206 on the handle 1204 such that pulling on the wire will cause the delivery catheter 1200 to bend at the tip. This steering mechanism may be used to steer the delivery catheter 1200 in place of the guide wire 1304.

In a typical embodiment, the delivery catheter 1200 is advanced over the guide wire 1304, or steered by the mechanism above, to a correct anatomical location such as, for example, a mitral valve annulus. Once at the correct site, the outer sheath catheter 1308 is retracted in a proximal direction relative to other catheters by turning a thumbwheel such as, for example, the thumbwheel 1206 on the handle 1204. As the sheath catheter 1308 is retracted the valve is uncovered and begins to deploy. Continued deployment is achieved by continued retraction of the sheath catheter 1308 in the direction of the arrows 1314 shown in FIG. 13A. Once satisfactory position has been confirmed by the operator the valve is released from the delivery catheter 1200 by retracting the hub catheter 1306 relative to the inner catheter 1302 in the direction of the arrows 1314 thereby uncovering the mating features and allowing complete release of the valve. The delivery catheter 1200 is then withdrawn from the patient.

In the example of FIGS. 13A and 13B, retraction of the sheath catheter 1308 in the direction of the arrows 1314 uncovers a ventricular portion of the valve prosthesis first and an atrial portion of the valve is the last to deploy. The mating feature acts to retain the valve at its atrial end before final release of the valve prosthesis. In other embodiments, the delivery catheter 1200 may be modified so that the valve deploys in an opposite direction. That is the atrial portion is uncovered first followed by the ventricular portion of the valve. In this arrangement, the sheath catheter 1308 is advanced in the distal direction. Still further modifications of the delivery catheter 1200 allow the retaining feature to be relocated to the distal end of the catheter so that it mates with the ventricular end of the valve.

In a typical embodiment, the delivery catheter 1200 is configured for delivery of a self expanding valve prosthesis. However, in various embodiments, the delivery catheter 1200 may be still further modified to facilitate delivery of a balloon expandable valve prostheses. In this case the mitral valve prosthesis is crimped onto a balloon at the distal end of the delivery catheter 1200. As a balloon expandable prosthesis will not self expand, there is no need for an outer sheath catheter 1308 to retain the valve prosthesis on the delivery catheter system 1200. However, the valve may optionally be covered by the outer sheath catheter 1308 for protection during delivery. Once the delivery catheter 1200 has been directed to the correct anatomical location such as, for example, the mitral valve annulus, the valve is deployed by retraction of the sheath catheter 1308, if present, followed by expansion of the balloon. The balloon is then deflated and the delivery catheter 1200 is withdrawn from the patient.

Figure 14:
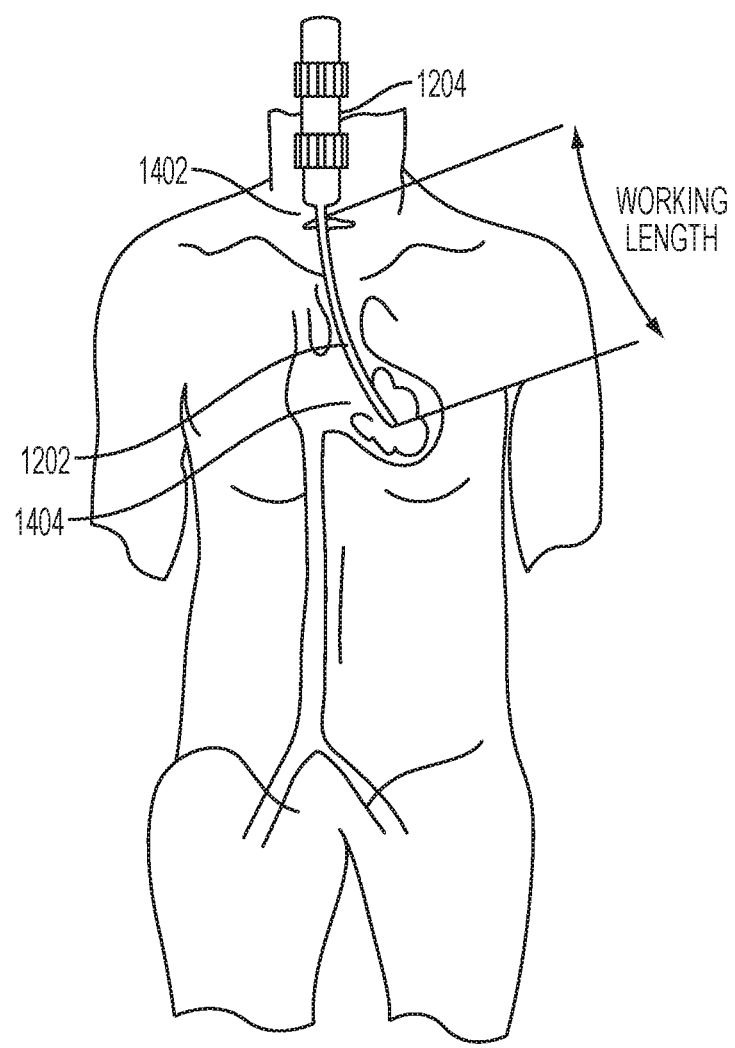
FIG. 14 is a diagrammatical illustration of a delivery catheter in use according to an exemplary embodiment.

FIG. 14 shows the delivery catheter 1200 that has been designed for delivery and deployment of a transcatheter mitral valve prosthesis by the Transcervical (Suprasternal) Approach (1). A similar working length is required for the other methods of mitral valve intervention proposed in this application.

In a typical embodiment, the working length of the delivery catheter 1200 is the distance from the tip of the catheter to the handle 1204. In a typical embodiment, the minimum working length for a delivery catheter 1200 to be used with this method is the length from just beyond the anatomical location of the mitral valve 1404 to the skin incision 1402. Too much working length outside of the skin incision 1402 makes the catheter 1200 unwieldy and difficult to manipulate or accurately control during use. A comfortable working length of 15-52 cm is desirable with this method. Notably, much less working length is required in this new method than would be required for a delivery catheter designed to be used with femoral venous (transseptal) method of access because the distance to the mitral valve from the femoral vein is much greater.

In a typical embodiment, closure devices may be adapted for this approach. An example of a closure device that may be adapted for use with this method is the FastSeal Bioabsorbable vascular access closure system manufactured by Vascular Closure Systems Inc. or the FastSeal Nitinol clip vascular access closure system manufactured by the same company. In a typical embodiment, a length of the delivery system for such closure devices exhibits sufficient length between the tip of the delivery system and the operating controls so that the controls are outside of the incision and accessible to the operator. In a typical embodiment, the length is at least 20 cm. In a typical embodiment, the depth of the closure device accommodates the thickness of the wall of the left atrium, which wall is typically 3-6 mm compared with the thickness of the left ventricle which wall is typically much thicker or the thickness of the wall of an artery, which wall is typically much thinner. In a typical embodiment, the diameter of the closure device accommodates opening in the left atrium required for the delivery of transcatheter mitral valve prostheses. That is, the closure device may be adapted to plug or crimp or suture the left atrial wall.

Transcervical Approach to the Abdominal or Thoracic Aorta

Stent Grafts and Access Routes to the Aorta

A stent graft is composed of a tubular supportive metal web like structure, the stent portion, covered by a special biocompatible fabric such as woven polyester or expanded polytetrafluoroethylene (ePTFE), the graft portion. The primary use of these devices is to support the weakened walls of the aorta and thereby prevent further expansion or rupture of the aorta. To be effective, the stent graft needs to be deployed inside the diseased segment of the aorta, such that it runs the entire length of the pathological segment, plus an extra distance of healthy vessel wall on either side in order for the device to be attached and for there to be no leakage around the prosthesis. The areas of healthy tissue required for attachment are termed "landing zones".

During an endovascular procedure, a stent graft is inserted into the body and delivered to the pathological segment of the aorta endovascularly. Almost universally access for aortic stent grafts into the circulation is via one or often both Femoral Arteries. The stent graft is then passed through a catheter, over a guide wire against the flow of blood, that is retrograde, into the external iliac artery and then on into the abdominal aorta, descending thoracic aorta, aortic arch and even ascending aorta, as required.

Stent grafts come in a variety of configurations to fit the anatomy of the patient and the particular location requiring treatment. The main body of the stent graft can also come in several variations, either multipiece, or single piece designs. These different designs allow for the treatment of pathologies in the aortic arch, descending thoracic aorta, abdominal aorta, iliac or femoral arteries or other arterial branches.

The existing access route via the iliac arteries or femoral arteries may take time to heal especially if an open incision is made to expose the artery because the groin has a relatively poor blood supply. The local blood supply may be further compromised by atherosclerotic disease affecting the lower limb vessels. The femoral region of skin is considered a "dirty" area from the point of view of intervention or surgery because of the risk of contamination of the wound by organisms colonizing the adjacent perineum. There is therefore a risk of wound infection at the femoral access site.

After closure of the femoral artery the patient is generally require to lie flat for a number of hours with compression to the local area if a percutaneous closure method has been employed or without compression if surgical closure technique is employed as flexing the legs at the hip places tension on the wound with risk of early wound breakdown or major haemorrhage. As tension is placed on the wound during ambulation it can be quite sore and uncomfortable for patients as they do begin to mobilize. All of this means patients require additional time before they can be discharged from hospital.

The iliac and femoral arteries are frequently affected by atherosclerosis which may be occlusive, partially occlusive or exhibit calcification rendering the arteries non-compliant. In these patients the femoral arteries are considered unsuitable for introduction of an aortic stent graft into the aorta. Because the diameter of the aorta is much greater than other arteries and because the nature of most aortic pathologies requires a covering of the stent, aortic stent grafts are much larger bulkier devices than uncovered, smaller stents used to treat occlusive disease in smaller arteries in the body. Therefore, in some patients the size of the femoral arteries may be small in relation to the size of the endovascular stent graft that needs to be passed through them, rendering such patients unsuitable for EVAR or TEVAR procedures. Furthermore, the need to compress endovascular stent grafts into dimensions suitable for access through the femoral arteries places a major restriction on the design of suitable stent grafts. This is especially important when one considers the design of stent grafts for treating complex pathologies where fenestrated or branched grafts may be required. Therefore, the current access route places restriction on the size of device, in the compressed state, that can be introduced into the aorta.

A further major problem of the existing Femoral Artery approach is access to the ascending aorta. Delivery of endovascular devices into the ascending aorta or proximal aortic arch requires bulky endovascular devices to be passed around the entire arch of the aorta where they may dislodge debris causing embolic material to become free in the circulation and potentially causing an acute embolic ischaemic event in a distal organ or stroke. As such patients frequently have plaque disease in the arch, this is a very considerable concern. Where the treatment indication is a dissection of the aorta, the inner lining of the arch may be very friable, especially if the arch itself is dissected. In such patients it would be very dangerous to pass bulky stent graft around the arch to access the ascending aorta as this would expose the patient to risk of rupture of the arch which could be fatal. Hence most ascending aortic pathologies are treated by open surgery at the current time.

Many patients presenting with dissection of the ascending aorta may also exhibit a degree of cardiac tamponade, a dangerous accumulation of fluid around the heart that impairs filling of the heart during diastole. At the current time, relief of cardiac tamponade requires open surgery or placement of a pericardiocentesis catheter percutaneously.

Because aneurysms can run past the length of the aorta into the iliac bifurcation, many stent grafts come with iliac leg extensions. One or both legs can be attached to the main body grafts, and similar to main body stent grafts, these extensions are available in a variety of diameters and lengths. Treatment of patients requiring aorto-bifemoral grafts currently requires access of both femoral arteries simultaneously, and assembly of the modular stent graft in vivo through complex, retrograde manipulations. Implantation of a bifurcated graft from the femoral route can take up to 3 hours in a vascular intervention suite and involve a team of as many as 12 persons. Indeed, deployment of the iliac limbs is complicated with this approach and this part of the procedure alone can take up to one hour. Stent grafts with iliac extensions usually require access to BOTH Femoral Arteries and the requirement to assemble in vivo adds further complexity to the endovascular procedure.

Diseased segments of aorta frequently extend close to important branch vessels, such as the renal arteries in the abdominal aorta or the branches of the aortic arch which supply the upper body in the thoracic aorta. The effect of this is to limit the length of landing zone available for attachment. Inadvertent coverage of important branch vessels during deployment is likely to lead to ischaemia and end organ failure of tissues supplied by those branches. Accurate positioning of aortic stent grafts from the Femoral Artery is made more difficult as the deployment site gets closer to the heart because of the pulsatile nature of cardiac output. Indeed, deployment of transcatheter aortic valves at the very origin of the aorta requires temporary cessation of the circulatory output by rapid ventricular pacing. Control of endovascular stent graft deployment is especially difficult in the thoracic aorta because of the distance of the guide wire and catheter from the point of entry into the circulation and because the wire has passed around the curve of the aortic arch making fine tuning of the stent graft position from the Femoral Arteries very difficult. When landing zones are short and in close proximity to important branches, very accurate positioning of stents during deployment of stents is required. Accurate positioning during deployment using the existing access approach is a particular problem for treatment of pathologies in the proximal thoracic aorta and for treatment of juxtarenal aneurysms of the abdominal aorta.

Important branches of the abdominal aorta, such as the renal arteries, arise at an acute angle to the direction of flow of blood through the aorta, making passage of guide catheters and/or stent graft deployment into the renal arteries themselves difficult from the retrograde, femoral arterial approach. It would be preferable if these vessels could be approached in an antegrade direction. This is a particular problem in the development of devices and methods for the deployment of fenestrated and branched stent grafts for treating complex pathologies involving the branch vessels, if the retrograde femoral approach is relied upon for delivery of such devices.

Treatment of pathologies in the aortic arch may require hybrid or debranching procedures to be performed on the branch vessels arising from the aortic arch at the time of stent graft placement. It would be preferable if these concomitant procedures could be performed through a single access site at the same time as endovascular intervention.

The inventors have also devised a new method for placing a stent in the abdominal or thoracic aorta or one of the aortic branches. This method accesses the aorta via the suprasternal notch. One mode of carrying out this method is set out below. The approach involves passing a catheter with rigid or semi-rigid inner trocar into an area packed with major vascular structures and the heart itself.

Figure 11:
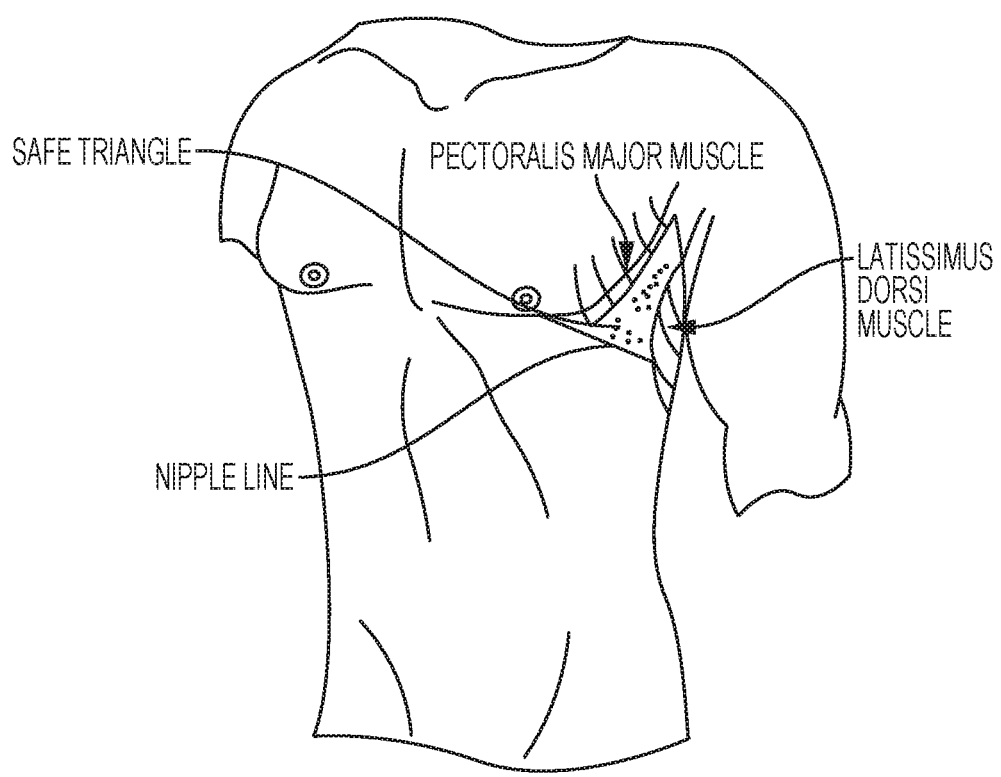
FIG. 11 shows the anatomical boundaries of the 'safe triangle' that is the recommended for entry site for insertion of a catheter into the chest cavity so as to avoid injury to organs or major blood vessels.

Like the mitral valve methods described above, the method devised by the inventors is surprisingly effective given current teaching in the field against the use of trocars in catheters into the chest. This teaching in the art also advises against inserting catheters into the chest outside of the 'safe triangle' defined by the anterior border of latissimus dorsi muscle, the lateral border of pectoralis major muscle and an imaginary horizontal line from the level of the nipple. The borders of the 'safe triangle' are shown in FIG. 11.

By way of background, in 2008 the UK National Patient Safety Agency (NPSA) reported 12 incidents of catheters being inserted into the chest resulting in death or severe harm to patients. The cause of deaths cited in the report included perforation of or trauma to the heart or blood vessels (NPSA Rapid Response Report Reference NPSA/ 2008/RRR03). Local policies in UK hospitals have since been drafted governing the insertion of catheters into the chest. For example, the Newcastle upon Tyne Hospitals NHS Foundation Trust Policy explicitly states "Trocar should NOT be used for insertion of cannula (catheters) into the chest".

The Advanced Trauma Life Support (ATLS) course manual of the American College of Surgeons (Ninth edition, 2012) offers consistent advice. The recommended site for insertion of a catheter into the chest is at the level of the nipple (fifth intercostal space), just anterior to the midaxillary line, which is within the 'safe triangle'. It also recommends the use of blunt dissection and insertion of a gloved finger into the incision to avoid injury to other organs rather than the steps proposed in this new method.

This new method of directing a catheter towards the aorta or towards the left atrium, in some instances directly towards the major intra-thoracic blood vessels (the aorta, the superior vena cava and the right pulmonary artery) is very much contrary to current teaching in the field.

FIG. 11 shows the 'safe triangle' recommended point of entry for a catheter being inserted into the chest. The safe triangle is bordered by the anterior border of latissimus dorsi muscle, the lateral border of pectoralis major muscle and an imaginary horizontal line from the level of the nipple (fifth intercostal space).

In a typical embodiment, the skin of the neck above the suprasternal notch is incised for percutaneous entry. A catheter is advanced inferiorly under the sternal notch into the mediastinum towards the aorta. In a typical embodiment, the catheter passes anterior or posterior to the innominate (left brachiocephalic) vein (preferably passes posterior to innominate vein).

In various embodiments, the pericardium may be opened to gain access to the ascending aorta or left intact for access to the distal ascending aorta and aortic arch or branches of the aortic arch. In a typical embodiment, a trocar or needle means is advanced into the aorta through the catheter. An example of a suitable point of entry into the aorta from the transcervical access method is marked with an 'x' in FIG. 8. However, the point of entry may be in the aortic arch, in one of the branch vessels from the arch or the ascending aorta. In various embodiments, the pericardium can also be opened to allow entry into the aorta.

In a typical embodiment, a guide wire is inserted through the trocar or needle into the aorta. The guide wire and the catheter are directed distally into the descending thoracic aorta and beyond or proximally into the ascending aorta.

In a typical embodiment, a dilator located inside an associated sheath introducer having a hemostasis valve is channelled over the guide wire. The dilator is then removed and a delivery catheter is inserted through the hemostasis valve and sheath introducer into the aorta. Once the catheter is positioned correctly for surgery, the catheter is secured with a catheter positioning device such as the one described above and shown in FIG. 9.

In a typical embodiment, an endovascular procedure is performed by passing repair devices such as, for example, stents or other grafts over the guide wire or through catheter. For example, a stent is loaded and compressed into a delivery configuration and inserted into the delivery catheter. The delivery catheter may then be routed through the aorta to the target site. Once the repair device is deployed in the correct position within the aorta, the sheath is withdrawn to expose the stent graft. At this stage the proximal end of the stent graft is retained by a capsule and a trigger wire. Next a trigger wire release mechanism is operated from the distal end of the stent graft. The capsule from the distal end is then withdrawn so that the distal end of the stent is deployed. The trigger wire is removed from the proximal end which releases the mooring loops and the graft is then fully deployed. The deployment device is then removed.

In various embodiments, the sheath and trigger wires may be arranged so that the proximal end of the stent is deployed first. This may be desired for accurate deployment at proximal landing zones.

In a typical embodiment, a purse string is inserted into the aorta around the site of entry. Alternatively a catheter based closure device may be used to close the aorta In a typical embodiment, the guide wire or catheter is withdrawn from the aorta. The opening in the aorta is then closed. In a typical embodiment, the guide wire or catheter is withdrawn from the patient and the skin wound is closed.

In a typical embodiment, local anaesthetic is instilled into the wound. In a typical embodiment, oral analgesics are prescribed as required.

In various embodiments, exposure of the aorta may be enhanced by inserting a retractor under the sternum and elevating the sternum. In various embodiments, direct visualisation of the aorta may be enhanced by illumination from one or more lights on the retractor. Alternatively, a retractor may be introduced under the sternum and the sternum elevated to allow the catheter to be passed under direct vision or with the aid of an endoscope. In various embodiments, the catheter may be advanced under visualisation through use of a rigid or flexible endoscope, introduced through the same incision with the image preferably displayed upon a screen directly above the incision for ease of use.

Figure 8:
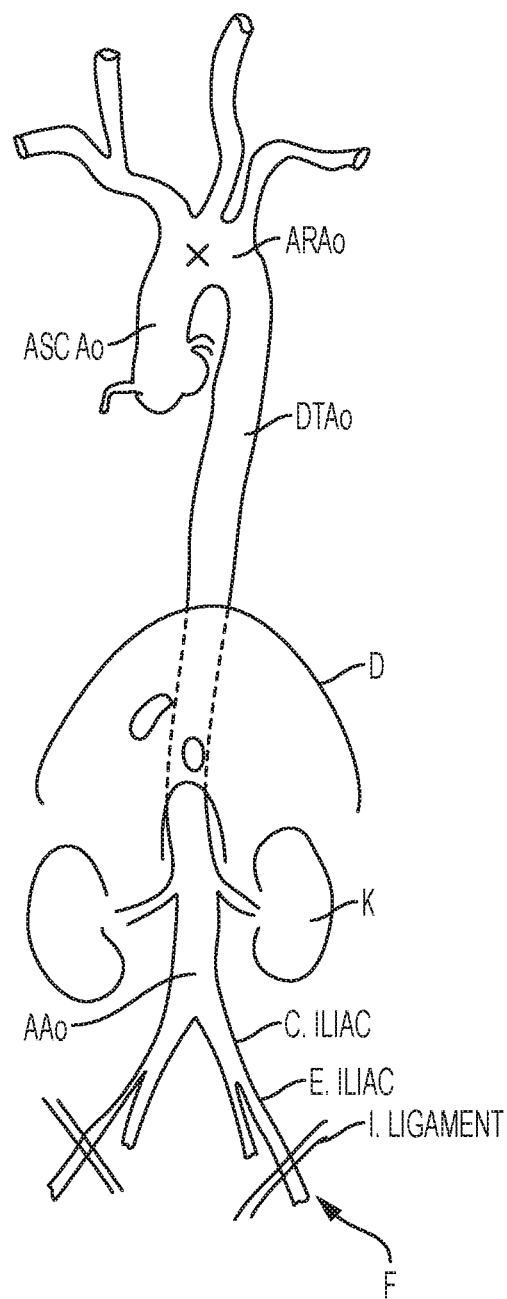
FIG. 8 is a diagrammatic illustration of the aorta showing the ascending aorta (Asc Ao), aortic arch (ARAo), descending thoracic aorta (DTAo), the diaphragm separating thoracic from abdominal portions of the aorta (AAo), the abdominal aorta (AAo), the common iliac arteries (C, ILIAC), external (E.ILIAC) and internal iliac arteries. The external iliac artery becomes the femoral artery (F) as it cross the inguinal ligaments (I.LIGAMENT). The mark 'x' is a possible entry point into the aorta using the transcervical approach method according to an exemplary embodiment.

FIG. 8 shows the ascending aorta (Asc Ao), aortic arch (ARAo), descending thoracic aorta (DTAo), the diaphragm (D) separating thoracic from abdominal portions of the aorta, the abdominal aorta (AAo), the common iliac arteries (C, ILIAC), external (E.ILIAC) and internal iliac arteries. The external iliac artery becomes the femoral artery (F) as it cross the inguinal ligaments (IL). The mark 'x' is a possible entry point into the aorta using the transcervical approach method.

Incisions in the neck are known to heal quickly because the body's rich vascular supply to the head and neck region. This region is also considered a 'clean' area as it is generally colonised by relatively harmless skin commensals. Accordingly, wound infections in this region are rare.

Incisions in the neck cause little pain relative to other incisions and are therefore well tolerated by patients. In particular, local anaesthesia is effective in rendering such incision pain free for the perioperative period. Thereafter, simple over the counter analgesia such as Paracetamol (Acetaminophen) are usually sufficient to control any residual pain from such wounds. Ambulation does not cause pain in this region.

Rapid healing and relative freedom from pain means that patients who have undergone endovascular procedures performed through the neck may be discharged on the day of surgery i.e. as 'day cases' or after a very limited number of days in hospital causing operational efficiencies and savings for the hospital and/or payment providers.

The presence of atherosclerosis whether occlusive, partially occlusive or not occlusive at all, the presence of calcification or the presence of tortuosity of the iliac or femoral arteries becomes irrelevant to the introduction of endovascular devices into the aorta because the access site is in the arch of the aorta or ascending aorta, remote from the ileo-femoral vessels.

The aorta is such a large caliber vessel that there is much less restriction on the size of devices that can be inserted through openings in the vessel. Direct entry into the thoracic aorta permits easy delivery of bulky, large caliber devices directly into the aorta, as their size is not restricted by the much smaller size of the femoral arteries and is not restricted by the presence of calcification, tortuosity, or occlusive disease of the femoral arteries or the same of the common and external iliac arteries from which the femoral arteries arise.

The aorta is a very large caliber vessel and is never occluded so it is always available for access. Therefore, this is an access route that can be relied upon when speed is of the essence and there is insufficient time to accurately evaluate this iliac and femoral arteries for suitable access route, as for example in the emergency repair of ruptured abdominal aortic aneurysm, AAA.

Reintervention through the transcervical direct aortic approach is likely to be easier and more forgiving than through distant, femoral vessels that have become fibrosed and/or friable from previous interventions. In a typical embodiment, repeat intervention are easily possible because there is no need to enter the aorta through the same point of entry utilized on previous occasions. A large amount of aorta accessible by this route allows the surgeon to choose a point of entry distinct from the previous entry point.

In a typical embodiment, a trocar, needle means or catheter may easily be advanced into the ascending aorta from this access site. Direct access to the aorta through the transcervical approach provides opportunity for endovascular repair of the ascending aorta which previously has been very difficult. Direct entry into the ascending aorta or proximal aortic arch obviates the need to pass bulky endovascular devices around the entire arch of the aorta where they may dislodge debris causing embolic material to become free in the circulation and potentially causing an acute embolic ischaemic event in a distal organ or stroke, if that organ is the brain. This is also pertinent in aortic dissection where the arch itself may be involved in the dissection process or there is a risk of further damaging the aorta potentially causing rupture which may be fatal.

Furthermore, opening the pericardium through the same incision can permit the relief of cardiac tamponade, a dangerous accumulation of fluid around the heart that impairs filling of the heart during diastole which frequently accompanies acute dissection of the ascending aorta.

Antegrade delivery of endovascular devices into the aorta from the transcervical approach allows BOTH iliac arteries to be entered through a SINGLE access point, making EVAR procedures that require stent grafts to be placed into both arteries faster and simpler to perform.

The aorta is a short distance from the incision so the length of guide wire or catheter is short for optimal control during device delivery. Access to the aortic arch and the ability to select the access point by direct inspection of the aorta, with or without the additional aid of epiaortic echocardiographic scanning, allows the guide wire or the catheter to be advanced in an antegrade direction into the descending thoracic aorta, abdominal aorta, iliac arteries and femoral arteries or even beyond. Even over long distances, control is better because the devices are being advanced in the direction of blood flow. As major branches of the aorta such as the renal arteries come off the aorta at an acute angle, it is likely that entry of additional guide wires into these vessels for delivery of fenestrated grafts or grafts with side arms into the vessels will be easier than with the retrograde approach from the femoral arteries. Control is improved by the locking mechanism shown in FIG. 9 to hold the catheter as this removes the human factor from the process of accurate device deployment. Proximity to the deployment site affords better control of the device during delivery for TEVAR ensuring accurate placement across tight landing zones. Antegrade delivery affords better control of the device during delivery for EVAR and TEVAR (descending thoracic aorta and arch only) ensuring accurate placement across tight landing zones.

The antegrade approach allows guide wires and delivery and deployment of stent grafts into major vessels such as the renal arteries that arise at an acute angle to the flow of blood through the aorta. This facilitates placement of complex grafts such as fenestrated or branched grafts at these locations to treat complex aortic pathologies involving or in close proximity to branch vessels.

Close proximity to branch vessels of the aortic arch (brachiocephalic, left common carotid and left subclavian arteries) allows additional procedures to be performed on these structures at the same time and through the same incision. Procedures include hybrid procedures such as debranching that allow a stent graft to be placed across the arch of the aorta while maintaining perfusion to the head and neck.

Close proximity of the point of entry into the aorta to the skin allows conventional, tried and tested, closure techniques such as purse string suture to be utilized by the surgeon. These techniques provide more reliable closure than percutaneous closure techniques routinely employed in the femoral artery location and not risk the possibility of narrowing the vessel which is a potential problem with closure of access points in the smaller femoral artery.

Various surgical devices facilitate surgery via these new surgical approaches. Details of such devices are given below.

Catheter Holding Device

The catheter holding device detailed above and shown in FIG. 9 may also be used for the above method of inserting a stent via the transcervical approach.

Stent Grafts

A stent configured for antegrade delivery may be used in the described methods. In various embodiments, the stent itself is structured in such a way for antegrade delivery. For example, the stent includes a main trunk and openings off the main trunk to allow the channeling of further stents off the main trunk. Such stents are used, for example, where further stents need to be funneled into the iliac arteries. For antegrade delivery, these openings will be facing downwards, towards the legs of the patient on insertion.

In various embodiments, a capsule or sheath is used to aid delivery of the stent. These are elongate tubular members defining a lumen which receives the stent. In various embodiments, trigger mechanisms and delivery devices aid release of the stent from the catheter at the site of repair. These trigger mechanisms and delivery devices are set up so as to aid antegrade delivery.

In various embodiments, the stent is pre-mounted on the delivery catheter so that the stent is oriented for antegrade delivery into the aortic arch, descending thoracic aorta, or abdominal aorta, iliac branches or beyond to aid the surgeon. In various embodiments, the stent is pre-mounted on the delivery catheter so that the stent is oriented for retrograde delivery into the ascending aorta.

Catheter Systems

The catheter includes a nose cone at a distal end to aid atraumatic passage of the catheter through the vasculature.

Although various embodiments of the method and system of the present invention have been illustrated in the accompanying Drawings and described in the foregoing Specification, it will be understood that the invention is not limited to the embodiments disclosed, but is capable of numerous rearrangements, modifications, and substitutions without departing from the spirit and scope of the invention as set forth herein. It is intended that the Specification and examples be considered as illustrative only.

What is claimed is:

1. A method for accessing a mitral valve, the method comprising:
   forming a suprasternal incision;
   inserting a retractor into the suprasternal incision, the retractor adapted to elevate a sternum;
   illuminating, via at least one of the retractor and an endoscope introduced into the incision, an inside of the incision;
   opening a pericardium under visualization aided by at least one of the endoscope and the retractor;
   separating an aorta and a superior vena cava to facilitate access to a roof of a left atrium;
   illuminating, via at least one of the retractor and the endoscope, the roof of the left atrium;
   placing a suture into the left atrium under visualization aided by at least one of the retractor and the endoscope;

passing at least one of a guide wire and a catheter into the left atrium proximate the suture;
advancing at least one of the guide wire and the catheter through a mitral valve;
deploying a mitral valve repair device;
withdrawing the catheter or the guide wire;
securing the suture;
removing the retractor; and
closing the incision.

2. The method of claim 1, wherein the incision is superior to a sternal notch.

3. The method of claim 1, comprising inserting an endoscope into the incision, the endoscope being adapted to aid passage of instruments into the incision.

4. The method of claim 1, comprising utilizing a steering wire to direct at least one of the catheter and the guide wire towards the left atrium.

5. The method of claim 1, comprising utilizing a trocar to penetrate the left atrium.

6. The method of claim 1, comprising utilizing a trocar to penetrate the pericardium.

7. The method of claim 1, comprising:
reducing a pressure within the aorta; and
displacing the aorta.

8. The method of claim 7, wherein the displacement of the aorta is to the left.

9. The method of claim 1, wherein the suture is a purse string suture.

10. A method for accessing a mitral valve, the method comprising:
forming a suprasternal incision;
illuminating an inside of the incision;
opening a pericardium under visualization, aided by at least one of an endoscope and a retractor;
separating an aorta and a superior vena cava to facilitate access to a roof of a left atrium;
illuminating a roof of a left atrium;
placing a suture into the left atrium under visualization;
passing at least one of a guide wire and a catheter into the left atrium proximate the suture;
advancing at least one of the guide wire and the catheter through a mitral valve;
deploying a mitral valve repair device;
withdrawing the catheter or the guide wire;
securing the suture; and
closing the incision.

* * * * *